United States Patent
Afar et al.

(10) Patent No.: US 9,914,783 B1
(45) Date of Patent: Mar. 13, 2018

(54) ANTI-PD-1 ANTIBODIES AND THEIR USES

(71) Applicant: AbbVie Biotherapeutics Inc., Redwood City, CA (US)

(72) Inventors: Daniel E. H. Afar, Los Altos Hills, CA (US); Fiona A. Harding, Mountain View, CA (US); Josue Samayoa, San Mateo, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 15/704,296

(22) Filed: Sep. 14, 2017

Related U.S. Application Data

(60) Provisional application No. 62/394,314, filed on Sep. 14, 2016.

(51) Int. Cl.
*C07K 16/30* (2006.01)
*C07K 16/28* (2006.01)

(52) U.S. Cl.
CPC .......... *C07K 16/30* (2013.01); *C07K 16/2896* (2013.01); *C07K 2317/565* (2013.01); *C07K 2319/30* (2013.01)

(58) Field of Classification Search
CPC ............... C07K 16/30; C07K 16/2896; C07K 2319/30; C07K 2317/565
USPC .......................................... 424/133.1, 173.1
See application file for complete search history.

(56) References Cited

U.S. PATENT DOCUMENTS

| | | | |
|---|---|---|---|
| 5,629,204 | A | 5/1997 | Honjo |
| 5,698,520 | A | 12/1997 | Honjo |
| 6,808,710 | B1 | 10/2004 | Wood |
| 6,936,704 | B1 | 8/2005 | Freeman |
| 7,029,674 | B2 | 4/2006 | Carreno |
| 7,101,550 | B2 | 9/2006 | Wood |
| 7,105,328 | B2 | 9/2006 | Wood |
| 7,488,802 | B2 | 2/2009 | Collins |
| 7,521,051 | B2 | 4/2009 | Collins |
| 7,595,048 | B2 | 9/2009 | Honjo |
| 8,008,449 | B2 | 8/2011 | Korman |
| 8,168,757 | B2 | 5/2012 | Finnefrock |
| 8,354,509 | B2 | 1/2013 | Carven |
| 8,728,474 | B2 | 5/2014 | Honjo |
| 8,900,587 | B2 | 12/2014 | Carven |
| 8,952,136 | B2 | 2/2015 | Carven |
| 9,067,999 | B1 | 6/2015 | Honjo |
| 9,073,994 | B2 | 7/2015 | Honjo |
| 2002/0160000 | A1 | 10/2002 | Wood |
| 2004/0241745 | A1 | 12/2004 | Honjo |
| 2006/0210567 | A1 | 9/2006 | Collins |
| 2007/0202100 | A1 | 8/2007 | Wood |
| 2008/0025979 | A1 | 1/2008 | Honjo |
| 2008/0311117 | A1 | 12/2008 | Collins |
| 2009/0076250 | A1 | 3/2009 | Honjo |
| 2014/0199319 | A1* | 7/2014 | Seagal ................... C07K 16/00 424/141.1 |
| 2017/0151343 | A1 | 6/2017 | Gish |
| 2017/0151344 | A1 | 6/2017 | Gish |

FOREIGN PATENT DOCUMENTS

| | | |
|---|---|---|
| EP | 3026062 A1 | 6/2016 |
| WO | WO 2001/014557 A1 | 3/2001 |
| WO | WO 2002/079499 A1 | 10/2002 |
| WO | WO 2003/006636 A1 | 1/2003 |
| WO | WO 2003/042402 A2 | 5/2003 |
| WO | WO 2004/004771 A1 | 1/2004 |
| WO | WO 2004/056875 A1 | 7/2004 |
| WO | WO 2008/083174 A2 | 7/2008 |
| WO | WO 2008/156712 A1 | 12/2008 |
| WO | WO 2010/036959 A2 | 4/2010 |
| WO | WO 2015/181331 A1 | 12/2015 |
| WO | 2016106159 A1 | 6/2016 |

OTHER PUBLICATIONS

Lederman et al (Molecular Immunology 28:1171-1181, 1991).*
Li et al (Proc. Natl. Acad. Sci. USA 77:3211-3214, 1980).*
Bennett et al., 2003 "Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses," *J Immunol* 170:711-718.
Blank et al., 2004 "PD-L1/B7H-1 Inhibits the Effector Phase of Tumor Rejection by T Cell Receptor (TCR) Transgenic $CD8^+$ T Cells," *Cancer Res* 64(3): 1140-1145.
Blank et al., 2007 "Contribution of the PD-L1/PD-1 pathway to T-cell exhaustion: an update on implications for chronic infections and tumor evasion," *Cancer Immunol Immunother* 56(5):739-745.
Callahan et al., 2016 "Targeting T Cell Co-receptors for Cancer Therapy," *Immunity* 44(5):1069-1078.
Chemnitz et al., 2004 "SHP-1 and SHP-2 Associate with Immunoreceptor Tyrosine-Based Switch Motif of Programmed Death 1 upon Primary Human T Cell Stimulation, but Only Receptor Ligation Prevents T Cell Activation," *J Immunol* 173(2):945-954.
Chen et al., 2015 "Anti-PD-1/PD-L1 therapy of human cancer: past, present, and future," *J Clin Invest* 125(9):3384-3391.
Dahan et al., 2015 "FcγRs Modulate the Anti-tumor Activity of Antibodies Targeting the PD-1/PD-L1 Axis," *Cancer Cell* 28(3):285-295.
Dong et al., 1999 "B7-H1, a third member of the B7 family, co-stimulates T-cell proliferation and interleukin-10 secretion," *Nat Med* 5(12):1365-1369.
Dong et al., 2002 "Tumor-associated B7-H1 promotes T-cell apoptosis: A potential mechanism of immune evasion," *Nat Med* 8(8):793-800.
Dong et al., 2003 "B7-H1 pathway and its role in the evasion of tumor immunity," *J Mol Med* 81(5):281-287.
Freeman et al., 2000 "Engagement of the PD-1 Immunoinhibitory Receptor by a Novel B7 Family Member Leads to Negative Regulation of Lymphocyte Activation," *J Exp Med* 192(7): 1027-1034.

(Continued)

*Primary Examiner* — Lynn A Bristol
(74) *Attorney, Agent, or Firm* — Dechert LLP

(57) ABSTRACT

The present disclosure provides novel anti-PD-1 antibodies, compositions including the new antibodies, nucleic acids encoding the antibodies, and methods of making and using the same.

17 Claims, 7 Drawing Sheets

(56) References Cited

OTHER PUBLICATIONS

Figure 3A:
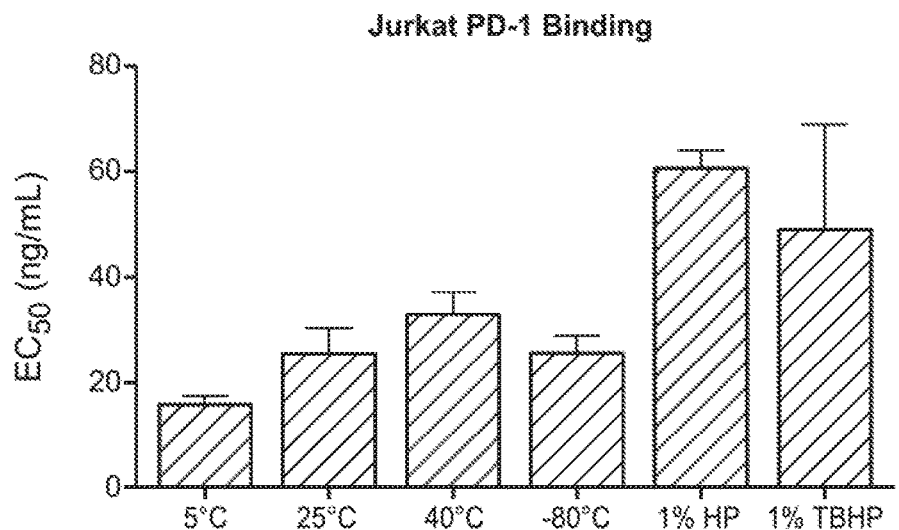

He et al., 2004 "Blocking Programmed Death-1 Ligand-PD-1 Interactions by Local Gene Therapy Results in Enhancement of Antitumor Effect of Secondary Lymphoid Tissue Chemokine," *J Immunol* 173(8).4919-4928.

Ishida et al., 1992 "Induced expression of PD-1, a novel member of the immunoglobulin gene superfamily, upon programmed cell death," *EMBO J* 11(11):3887-3895.

Iwai et al., 2002 "Involvement of PD-L1 on tumor cells in the escape from host immune system and tumor immunotherapy by PD-L1 blockade," *Pro Natl Acad Sci USA* 99(19): 12293-12297.

Iwai et al., 2005 "PD-1 blockade inhibits hematogenous spread of poorly inummogenic tumor cells by enhanced recruitment of effector T cells," *Int Immunol* 17(2):133-144.

Keir et al., 2008 "PD-1 and Its Ligands in Tolerance and Immunity," *Annu Rev Immunol* 26:677-704.

Konishi et al., 2004 "B7-H1 Expression on Non-Small Cell Lung Cancer Cells and Its Relationship with Tumor-Infiltrating Lymphocytes and Their PD-1 Expression," *Clin Cancer Res* 10(15):5094-5100.

Latchman et al., 2001 "PD-L2 is a second ligand for PD-1 and inhibits T cell activation," *Nat Immunol* 2(3):261-268.

Mandai et al., 2016 "Dual Faces of IFNγ in Cancer Progression: A Role of PD-L1 Induction in the Determination of Antitumor Immunity," Clin Cancer Res 22:2329-2334.

Okazaki et al., 2001 "PD-1 immunoreceptor inhibits B cell receptor-mediated signaling by recruiting src homology 2-domain-containing tyrosine phosphatase 2 to phosphotyrosine," *Proc Natl Acad Sci USA* 98(24):13866-13871.

Okazaki et al., 2002 "New regulatory co-receptors: inducible co-stimulator and PD-1," *Curr Opin Immunol* 41(6):779-782.

Panka et al., 1988 "Variable region framework differences result in decreased or increased affinity of variant anti-digoxin antibodies," *Immunology* 85:3080-3084.

Riley 2009 "PD-1 signaling in Primary T cells," *Immunol Rev* 229(1):114-125.

Rudikoff et al., 1982 "Single amino acid substitution altering antigen-binding specificity," *Proc Natl Acad Sci USA* 79:1979-1983.

Sanmamed et al., 2014 "Inducible Expression of B7-H1 (PD-L1) and Its Selective Role in Tumor Site Immune Modulation," *Cancer J* 20(4):256-261.

Sunshine et al., 2015 "PD-1/PD-L1 inhibitors," *Curr Opin Pharmacol* 23:32-38 (pp. 1-14).

Thompson et al., 2007 "PD-1 Is Expressed by Tumor-Infiltrating Immune Cells and Is Associated with Poor Outcome for Patients with Renal Cell Carcinoma," *Clin Cancer Res* 13(6):1757-1761.

Waldmann, 2006 "Effective cancer therapy through immunomodulation," *Annu Rev Med* 57(1):65-81.

Wong et al., 2007 "Programmed death-1 blockade enhances expansion and functional capacity of human melanoma antigen-specific CTLs," *Int Immunol* 19(10):1223-1234.

Yao et al., 2014 "PD-1 as an Immune Modulatory Receptor," *Cancer J* 20(4):262-264 (pp. 1-7).

Prescribing Information for Keytruda® (pembrolizumab) for injection, for intravenous use Initial U.S. Approval: 2014 (Revised: Jul. 2017), pp. 1-24.

Prescribing Information for Opdivo (nivolumab) injection, for intravenous use Initial U.S. Approval: 2014 (Revised: Dec. 2015), pp. 1-22.

Prescribing Information for Yervoy® (ipilimumab) injection, for intravenous use Initial U.S. Approval: 2011 (Revised: Oct. 2015), pp. 1-11.

Securities and Exchange Commission Form 8-K for Medivation, Inc. for the period ending Jan. 25, 2016, pp. 1-47.

U.S. Appl. No. 62/417,480, filed Nov. 4, 2016, pp. 1-200.
U.S. Appl. No. 62/261,092, filed Nov. 30, 2015, pp. 1-169.
U.S. Appl. No. 62/417,489, filed Nov. 4, 2016, pp. 1-167.
U.S. Appl. No. 62/261,114, filed Nov. 30, 2015, pp. 1-143.

\* cited by examiner

```
          10         20         30         40         50
  MQIPQAPWPV VWAVLQLGWR PGWFLDSPDR PWNPPTFSPA LLVVTEGDNA
          60         70         80         90        100
  TFTCSFSNTS ESFVLNWYRM SPSNQTDKLA AFPEDRSQPG QDCRFRVTQL
         110        120        130        140        150
  PNGRDFHMSV VRARRNDSGT YLCGAISLAP KAQIKESLRA ELRVTERRAE
         160        170        180        190        200
  VPTAHPSPSP RPAGQFQTLV VGVVGGLLGS LVLLVWVLAV ICSRAARGTI
         210        220        230        240        250
  GARRTGQPLK EDPSAVPVFS VDYGELDFQW REKTPEPPVP CVPEQTEYAT
         260        270        280
  IVFPSGMGTS SPARRGSADG PRSAQPLRPE DGHCSWPL
```
Human PD-1 (SEQ ID NO:1)

```
          10         20         30         40         50
  MWVRQVPWSF TWAVLQLSWQ SGWLLEVPNG PWRSLTFYPA WLTVSEGANA
          60         70         80         90        100
  TFTCSLSNWS EDLMLNWNRL SPSNQTEKQA AFCNGLSQPV QDARFQIIQL
         110        120        130        140        150
  PNRHDFHMNI LDTRRNDSGI YLCGAISLHP KAKIEESPGA ELVVTERILE
         160        170        180        190        200
  TSTRYPSPSP KPEGRFQGMV IGIMSALVGI PVLLLLAWAL AVFCSTSMSE
         210        220        230        240        250
  ARGAGSKDDT LKEEPSAAPV PSVAYEELDF QGREKTPELP TACVHTEYAT
         260        270        280
  IVFTEGLGAS AMGRRGSADG LQGPRPPRHE DGHCSWPL
```
Murine PD-1 (SEQ ID NO:2)

*FIG. 1A*

```
         10         20         30         40         50
MRIFAVFIFM TYWHLLNAFT VTVPKDLYVV EYGSNMTIEC KFPVEKQLDL
         60         70         80         90        100
AALIVYWEME DKNIIQFVHG EEDLKVQHSS YRQRARLLKD QLSLGNAALQ
        110        120        130        140        150
ITDVKLQDAG VYRCMISYGG ADYKRITVKV NAPYNKINQR ILVVDPVTSE
        160        170        180        190        200
HELTCQAEGY PKAEVIWTSS DHQVLSGKTT TTNSKREEKL FNVTSTLRIN
        210        220        230        240        250
TTTNEIFYCT FRRLDPEENH TAELVIPELP LAHPPNERTH LVILGAILLC
        260        270        280        290
LGVALTFIFR LRKGRMMDVK KCGIQDTNSK KQSDTHLEET
```

Human PD-L1 (SEQ ID NO:3)

```
         10         20         30         40         50
LQLHQIAALF TVTVPKELYI IEHGSNVTLE CNFDTGSHVN LGAITASLQK
         60         70         80         90        100
VENDTSPHRE RATLLEEQLP LGKASFHIPQ VQVRDEGQYQ CIIIYGVAWD
        110        120        130        140        150
YKYLTLKVKA SYRKINTHIL KVPETDEVEL TCQATGYPLA EVSWPNVSVP
        160        170        180        190        200
ANTSHSRTPE GLYQVTSVLR LKPPPGRNFS CVFWNTHVRE LTLASIDLQS
        210        220        230        240        250
QMEPRTHPTW LLHIFIPSCI IAFIFIATVI ALRKQLCQKL YSSKDTTKRP
        260
VTTTKREVNS AI
```

Human PD-L2 (SEQ ID NO:4)

FIG. 1B

Exemplary V$_H$ and V$_L$ sequences. CDRs underlined.

Mu12A11 V$_H$ (SEQ ID NO:31)

QIQLVQSGPELKKPGETVMISCKAS<u>GYTFTHYGMN</u>WVKQAPGKGLKWVG<u>WVNT
YTGEPTYADDFKG</u>RLAFSLETSASTAYLQINNLKNEDTATYFCT<u>REGEGMGFGDW
G</u>QGTTLTVSS

Mu12A11 V$_L$ (SEQ ID NO:41)

DVLMTQIPLSLPVSLGDQASISC<u>RSSQSIVHSHGDTYLE</u>WYLQKPGQSPKLLIY<u>KVS
NRFS</u>GVPDRFSGSGSGTDFTLKISRVEAEDLGVYYC<u>FQGSHIPVT</u>FGAGTKLEIK

Hu12A11.1b V$_H$ (SEQ ID NO:32)

EIQLVQSGSELKKPGASVKVSCKAS<u>GYTFTHYGMN</u>WVRQAPGQGLEWVG<u>WVNT
YTGEPTYADDFKG</u>RLVFSLDTSVSTAYLQISSLKAEDTAVYYCT<u>REGEGMGFGDW
G</u>QGTTVTVSS

Hu12A11.1b, Hu12A11.2b1, Hu12A11.2b2, Hu12A11.2b3, or Hu12A11.2b4 V$_L$
(SEQ ID NO:42)

DVVMTQSPLSLPVTPGEPASISC<u>RSSQSIVHSHGDTYLE</u>WYLQKPGQSPQLLIY<u>KVS
NRFS</u>GVPDRFSGSGSGTDFTLKISRVEAEDVGVYYC<u>FQGSHIPVT</u>FGQGTKLEIK

Hu12A11.2b1 V$_H$ (SEQ ID NO:33)

EIQLVQSGAEVKKPGSSVKVSCKAS<u>GYTFTHYGMN</u>WVRQAPGQGLEWVG<u>WVNT
YTGEPTYADDFKG</u>RLTFTLDTSTSTAYMELSSLRSEDTAVYYCT<u>REGEGMGFGDW
G</u>QGTTVTVSS

Hu12A11.2b2 V$_H$ (SEQ ID NO:34)

EIQLVQSGAEVKKPGSSVKVSCKAS<u>GYTFTHYGMN</u>WVRQAPGQGLEWVG<u>WVNT
YTGEPTYADDFKG</u>RLTFTLDTSTSTAYMELSSLRSEDTAVYYCT<u>REGEGIGFGDW
G</u>QGTTVTVSS

Hu12A11.2b3 V$_H$ (SEQ ID NO:35)

EIQLVQSGAEVKKPGSSVKVSCKAS<u>GYTFTHYGMN</u>WVRQAPGQGLEWVG<u>WVNT
YTGEPTYADDFKG</u>RLTFTLDTSTSTAYMELSSLRSEDTAVYYCT<u>REGEGVGFGDW
G</u>QGTTVTVSS

Hu12A11.2b4 V$_H$ (SEQ ID NO:36)

EIQLVQSGAEVKKPGSSVKVSCKAS<u>GYTFTHYGMN</u>WVRQAPGQGLEWVG<u>WVNT
YTGEPTYADDFKG</u>RLTFTLDTSTSTAYMELSSLRSEDTAVYYCT<u>REGEGLGFGDW
G</u>QGTTVTVSS

FIG. 2

ANTI-PD-1 ANTIBODIES AND THEIR USES

1. CROSS REFERENCE TO RELATED APPLICATIONS

This application claims the benefit under 35 U.S.C. § 119(e) of U.S. Provisional Application No. 62/394,314, filed Sep. 14, 2016, the contents of which are incorporated herein in its entirety by reference thereto.

2. SEQUENCE LISTING

The instant application contains a Sequence Listing which has been submitted electronically in ASCII format and is hereby incorporated by reference in its entirety. Said ASCII copy, created on Aug. 10, 2017, is named 381493-327US_SL.txt and is 32,733 bytes in size.

3. TECHNICAL FIELD

The present application pertains to, among other things, novel anti-PD-1 antibodies, compositions including the new antibodies, nucleic acids encoding the antibodies, and methods of making and using the same.

4. BACKGROUND

Cancer therapies comprise a wide range of therapeutic approaches, including surgery, radiation, and chemotherapy. While the various approaches allow a broad selection of treatments to be available to the medical practitioner to treat the cancer, existing therapeutics suffer from a number of disadvantages, such as a lack of selectivity of targeting cancer cells over normal, healthy cells, and the development of resistance by the cancer to the treatment.

Recent approaches based on targeted therapeutics, which interfere with cellular processes of cancer cells preferentially over normal cells, have led to chemotherapeutic regimens with fewer side effects as compared to non-targeted therapies such as radiation treatment.

Cancer immunotherapy has emerged as a promising therapeutic approach to complement existing standards of care. See, e.g., Miller, et al. Cancer Cell, 27, 439-449 (2015). Such immunotherapy approaches include the development of antibodies used to modulate the immune system to kill cancer cells.

For example, interaction of PD-1, a type I cell surface receptor, with either of its two ligands, PD-L1 or PD-L2, results in a dominant negative checkpoint signal that limits subsequent antigen receptor-driven cellular activation. The ligands for PD-1 are differentially expressed on various tissues and cell types, including antigen-presenting cells of the immune system, and are upregulated on many types of tumor cells. Upregulation of PD-L1 within the tumor microenvironment is a proposed mechanism of tumors to subvert protective anti-tumor immune responses by the host. Antibodies directed at PD-1 that block the interaction of the receptor with either of its ligands result in inhibition of negative signaling. In vitro inhibition of the PD-1 mediated checkpoint signal has been demonstrated to result in prolonged antigen-specific T cell activation. In vivo PD-1 blockade has been shown to enhance anti-tumor immune responses in both syngeneic mouse tumor models and in human clinical trials.

Anti-tumor immune responses in patients with solid tumors have been enhanced by anti-PD-1 treatment. There are two approved and marketed antagonistic anti-PD-1 monoclonal antibodies: nivolumab (OPDIVO®) and pembrolizumab (KEYTRUDA®), with approvals in the US and the European Union to treat diseases such as unresectable or metastatic melanoma and metastatic non-small cell lung cancer. Treatment of patients with these agents has resulted in anti-tumor responses as measured by improvement in either progression free survival and/or overall survival.

The recent failure of OPDIVO® to slow progression of advanced lung cancer in a treatment-naïve patient population in a clinical trial comparing OPDIVO® with conventional chemotherapy highlights the need for alternative approaches and additional cancer treatments to complement existing therapeutic standards of care.

5. SUMMARY

The present disclosure provides anti-PD-1 antibodies and binding fragments thereof that specifically bind to PD-1. The amino acid sequences of exemplary CDRs, as well as the amino acid sequence of the $V_H$ and $V_L$ regions of the heavy and light chains of exemplary anti-PD-1 antibodies are provided in the Detailed Description below. Antibodies provided herein interfere with the interaction of the PD-1 receptor with either of its ligands (PD-L1, SEQ ID NO:3; PD-L2, SEQ ID NO:4), resulting in inhibition of negative signaling and upregulation of the adaptive immune response.

The anti-PD-1 antibodies may include modifications and/or mutations that alter the properties of the antibodies, such as increase half-life, increase or decrease ADCC, etc., as is known in the art.

Nucleic acids comprising nucleotide sequences encoding the anti-PD-1 antibodies of the disclosure are provided herein, as are vectors comprising nucleic acids. Additionally, prokaryotic and eukaryotic host cells transformed with a vector comprising a nucleotide sequence encoding a disclosed anti-PD-1 antibody are provided herein, as well as eukaryotic (such as mammalian) host cells engineered to express the nucleotide sequences. Methods of producing antibodies, by culturing host cells and recovering the antibodies are also provided, and discussed further in the Detailed Description below.

In another aspect, the present disclosure provides compositions including the anti-PD-1 antibodies described herein. The compositions generally comprise one or more anti-PD-1 antibody as described herein, and/or salts thereof, and one or more excipients, carriers or diluents.

The present disclosure provides methods of treating subjects, such as human subjects, diagnosed with a solid tumor or a blood malignancy with an anti-PD-1 antibody. The method generally involves administering to the subject an amount of an anti-PD-1 antibody described herein effective to provide therapeutic benefit. The subject may be diagnosed with any one of a number of solid tumors or blood malignancies that may be newly diagnosed, relapsed, or relapsed and refractory. An anti-PD-1 antibody is typically administered as an intravenous infusion twice a week, once a week, once every two weeks, once every three weeks, once every four weeks, once every five weeks, once every six weeks, once every seven weeks, or once every eight weeks.

The anti-PD-1 antibodies may be administered as single therapeutic agents (monotherapy) or adjunctive to or with other therapeutic agents typically, but not necessarily, those used for the treatment of a solid tumor or blood malignancy. Therapeutic agents typically will be used at their approved dose, route of administration, and frequency of administration, but may be used at lower dosages.

The anti-PD-1 antibodies may be administered via a variety of routes or modes of administration, including but not limited to, intravenous infusion and/or injection, intratumoral injection, and subcutaneous injection. The amount administered will depend upon the route of administration, the dosing schedule, the type of cancer being treated, the stage of the cancer being treated, and other parameters such as the age and weight of the patient, as is well known in the art. Specific exemplary dosing schedules expected to provide therapeutic benefit are provided in the Detailed Description.

6. BRIEF DESCRIPTION OF THE FIGURES

FIGS. 1A-1B show the amino acid sequences of human PD-1 (SEQ ID NO:1), murine PD-1 (SEQ ID NO:2), human PD-L1 (SEQ ID NO:3), and human PD-L2 (SEQ ID NO:4). FIG. 1A depicts the sequences of human and murine PD-1; FIG. 1B depicts the sequences of human PD-L1 and PD-L2.

FIG. 2 provides amino acid sequences of $V_H$ and $V_L$ regions in exemplary anti-PD-1 antibodies of the disclosure.

Figure 3B:
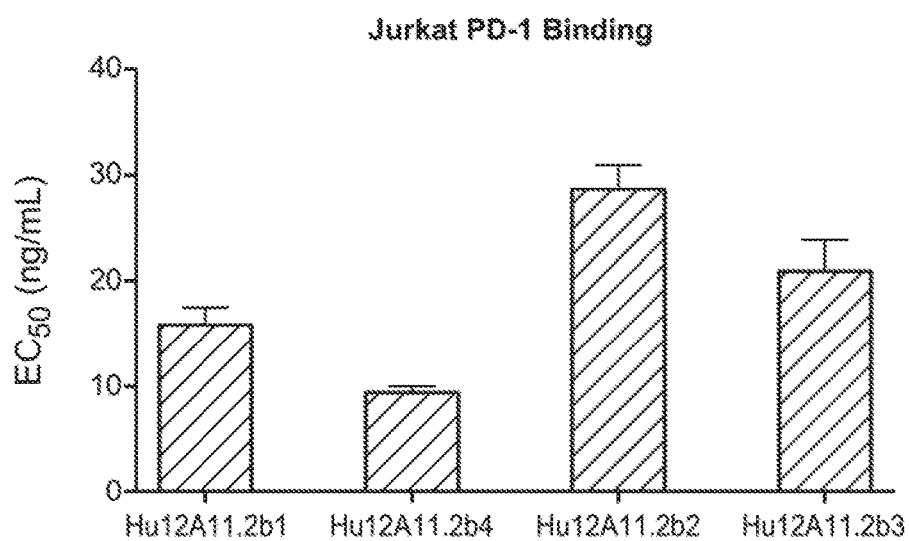
Figure 3C:
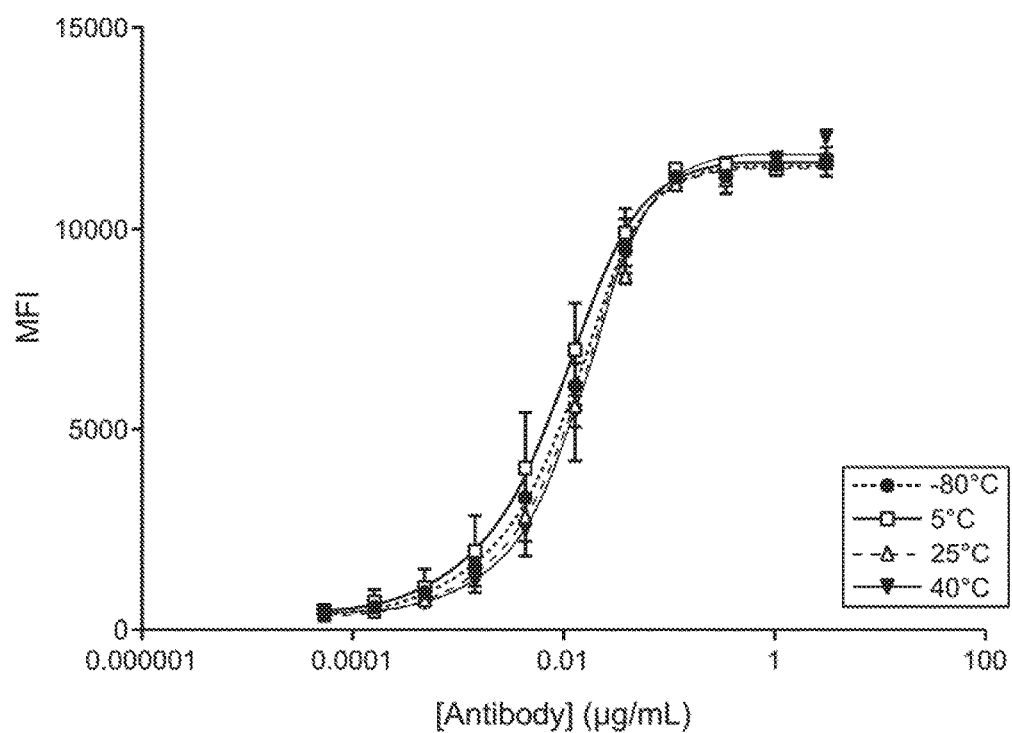

FIGS. 3A-3C show the effects of oxidative and variable temperature conditions on exemplary humanized antibody Hu12A11.2b1 and its point mutations at Kabat 99 in CDR-H3. FIG. 3A depicts binding to PD-1 in Jurkat cells of Hu12A11.2b1 stored at −80, 5, 25, or 40° C. for 30 days or after being subjected to oxidative conditions (1% hydrogen peroxide, "1% HP"; or 1% tert-butyl hydroperoxide, "1% TBHP"); FIG. 3B depicts binding of anti-PD-1 antibodies Hu12A11.2b1, Hu12A11.2b2, Hu12A11.2b3, and Hu12A11.2b4; FIG. 3C depicts the binding of Hu12A11.2b4 to PD-1 in Jurkat cells after incubation at −80, 5, 25, or 40° C. for 30 days.

Figure 4A:
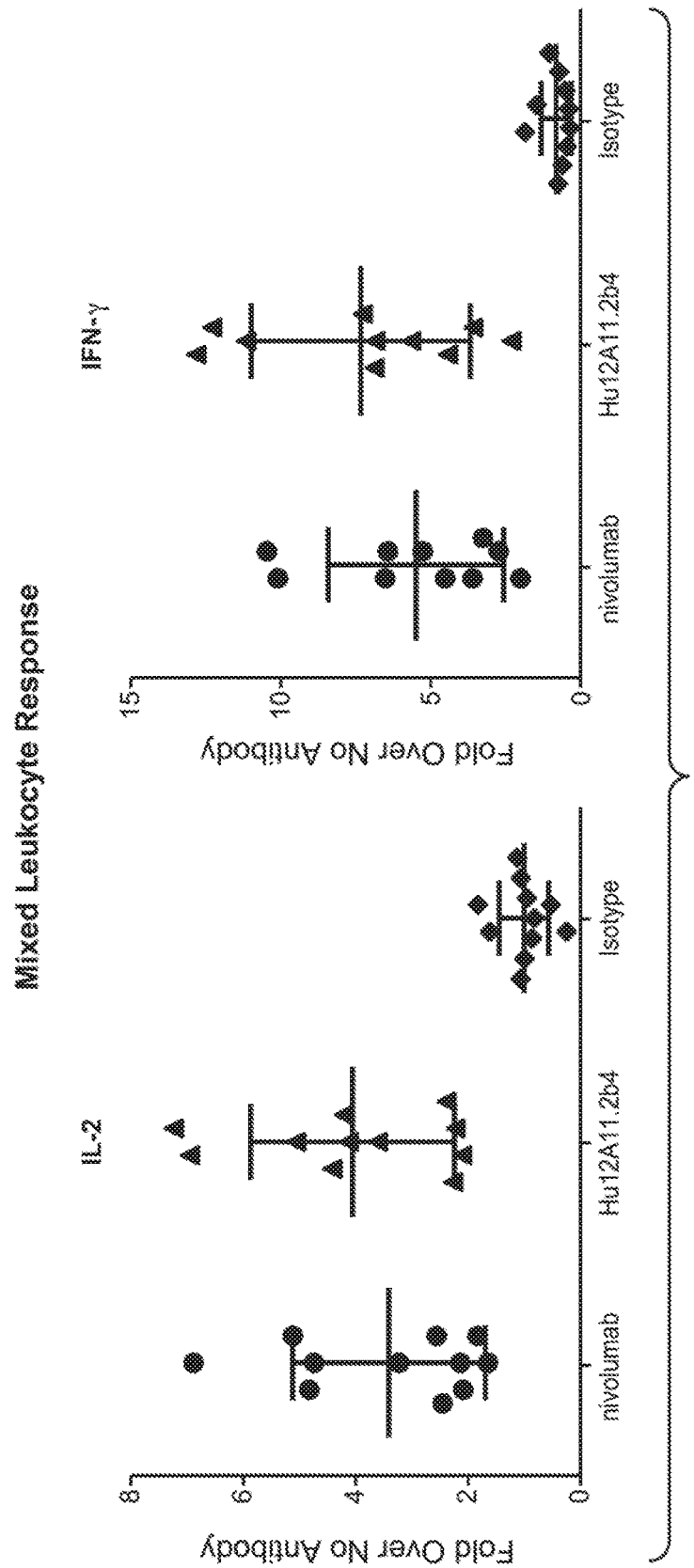
Figure 4B:
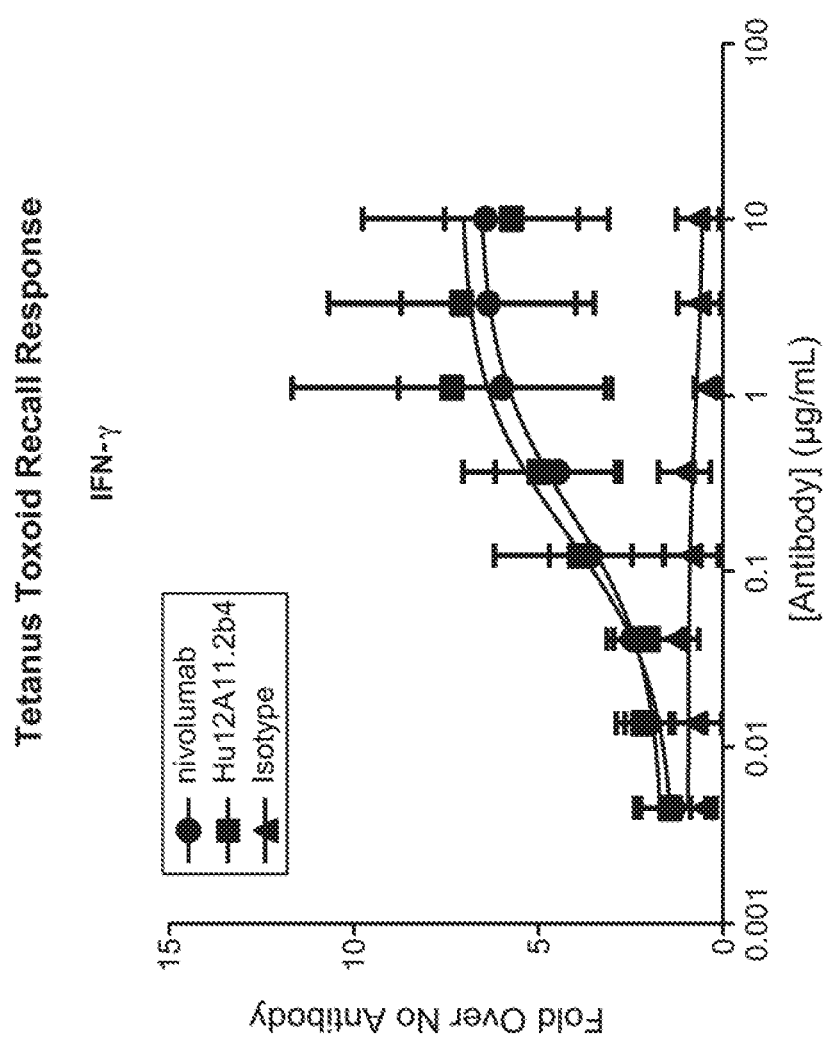

FIGS. 4A-4B show the biological activity of nivolumab and Hu12A11.2b4 in mixed leukocyte response (MLR) and tetanus toxoid antigen recall assays. FIG. 4A shows enhancement in IL-2 or interferon-gamma (IFN-γ) levels after treatment with 10 μg/mL of nivolumab, Hu12A11.2b4, or isotype control in mixed leukocyte cultures. FIG. 4B shows dose-dependent response of nivolumab, Hu12A11.2b4, or isotype control on IFN-γ enhancement in tetanus toxoid response assay.

7. DETAILED DESCRIPTION

The present disclosure concerns antibodies and fragments that specifically bind PD-1, compositions comprising the antibodies, polynucleotides encoding anti-PD-1 antibodies, host cells capable of producing the antibodies, methods and compositions useful for making the antibodies and binding fragments, and various methods of using the same.

As will be appreciated by skilled artisans, antibodies are "modular" in nature. Throughout the disclosure, various specific embodiments of the various "modules" composing the antibodies are described. As specific non-limiting examples, various specific embodiments of $V_H$ CDRs, $V_H$ chains, $V_L$ CDRs and $V_L$ chains are described. It is intended that all of the specific embodiments may be combined with each other as though each specific combination were explicitly described individually.

7.1. Abbreviations

The antibodies, binding fragments, and polynucleotides described herein are, in many embodiments, described by way of their respective polypeptide or polynucleotide sequences. Unless indicated otherwise, polypeptide sequences are provided in N→C orientation; polynucleotide sequences in 5'→3' orientation. For polypeptide sequences, the conventional three or one-letter abbreviations for the genetically encoded amino acids may be used, as noted in TABLE 1, below.

TABLE 1

| Encoded Amino Acid Abbreviations | | |
|---|---|---|
| Amino Acid | Three Letter Abbreviation | One-Letter Abbreviation |
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

| Encoded Amino Acid Classes | |
|---|---|
| Class | Amino Acids |
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

The abbreviations used for the various exemplary antibodies disclosed herein are provided in TABLE 3, below:

TABLE 3

Antibody Abbreviations

| Clone/Name | Abbreviation | V$_H$ Sequence (FIG. 2) | V$_L$ Sequence (FIG. 2) |
|---|---|---|---|
| Mouse 12A11 | Mu12A11 | Mu12A11 V$_H$ SEQ ID NO: 31 | Mu12A11 V$_L$ SEQ ID NO: 41 |
| Humanized 12A11.1b | Hu12A11.1b | Hu12A11.1b V$_H$ SEQ ID NO: 32 | Hu12A11.1a V$_L$ SEQ ID NO: 42 |
| Humanized 12A11.2b with mouse CDRs | Hu12A11.2b1 | Hu12A11.2b V$_H$ SEQ ID NO: 33 | Hu12A11.1a V$_L$ SEQ ID NO: 42 |
| Humanized 12A11.2b with M99I in CDR-H3 | Hu12A11.2b2 | Hu12A11.2b V$_H$ SEQ ID NO: 34 M99I variant | Hu12A11.1a V$_L$ SEQ ID NO: 42 |
| Humanized 12A11.2b with M99V in CDR-H3 | Hu12A11.2b3 | Hu12A11.2b V$_H$ SEQ ID NO: 35 M99V variant | Hu12A11.1a V$_L$ SEQ ID NO: 42 |
| Humanized 12A11.2b with M99L in CDR-H3 | Hu12A11.2b4 | Hu12A11.2b V$_H$ SEQ ID NO: 36 M99L variant | Hu12A11.1a V$_L$ SEQ ID NO: 42 |

7.2. Definitions

Unless otherwise defined herein, scientific and technical terms used in connection with the present disclosure shall have the meanings that are commonly understood by those of ordinary skill in the art.

7.3. Anti-PD-1 Antibodies and Binding Fragments

In one aspect, the disclosure concerns antibodies and/or binding fragments thereof that specifically bind programmed cell death protein 1 (PD-1) receptor (also known as PDCD1, CD279, PD1, SLEB2, or SLE1).

As used herein, the term "antibody" (Ab) refers to an immunoglobulin molecule that specifically binds to a particular antigen—here, PD-1. In some embodiments, the anti-PD-1 antibodies of the disclosure bind to human PD-1 and thereby modulate the immune system. The resulting immune system response is cytotoxic to tumor cells. Anti-PD-1 antibodies of the disclosure comprise complementarity determining regions (CDRs), also known as hypervariable regions, in both the light chain and the heavy chain variable domains. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The disclosure provides antibodies comprising modifications in these hybrid hypervariable positions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the target binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

The antibodies of the disclosure may be polyclonal, monoclonal, genetically engineered, and/or otherwise modified in nature, including but not limited to chimeric antibodies, humanized antibodies, human antibodies, single chain antibodies, etc. In various embodiments, the antibodies comprise all or a portion of a constant region of an antibody. In some embodiments, the constant region is an isotype selected from: IgA (e.g., IgA$_1$ or IgA$_2$), IgD, IgE, IgG (e.g., IgG$_1$, IgG$_2$, IgG$_3$ or IgG$_4$), and IgM. In specific embodiments, the antibodies described herein comprise an IgG$_1$. In other embodiments, the anti-PD-1 antibodies comprise an IgG$_2$. In yet other embodiments, the anti-PD-1 antibodies comprise an IgG$_4$. As used herein, the "constant region" of an antibody includes the natural constant region, allotypes or natural variants, such as D356E and L358M, or A431G in human IgG$_1$. See, e.g., Jefferis and Lefranc, MAbs, 1(4): 332-338 (July-August 2009).

The light constant region of an anti-PD-1 antibody may be a kappa (κ) light region or a lambda (λ) region. A λ light region can be any one of the known subtypes, e.g., λ$_1$, λ$_2$, λ$_3$, or λ$_4$. In some embodiments, the anti-PD-1 antibody comprises a kappa (κ) light region.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of the anti-PD-1 antibodies in humans, chimeric, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585,089; 5,693,761; 5,693,762; and U.S. Pat. No. 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332.

"Human antibodies" include antibodies having the amino acid sequence of a human immunoglobulin and include antibodies isolated from human immunoglobulin libraries or from animals transgenic for one or more human immunoglobulins and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598. In addition, companies such as LakePharma, Inc. (Belmont, Calif.) or Creative BioLabs (Shirley, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

Anti-PD-1 antibodies of the disclosure include full-length (intact) antibody molecules.

In some embodiments, the present disclosure also includes anti-PD-1 binding fragments that are capable of specifically binding PD-1. Examples of antibody binding fragments include by way of example and not limitation, Fab, Fab', F(ab')$_2$, Fv fragments, single chain Fv fragments and single domain fragments.

An Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_2$ fragments lack the Fc fragment of an intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define a target binding site on the surface of the $V_H$-$V_L$ dimer. Often, the six CDRs confer target binding specificity to the antibody. However, in some instances even a single variable domain (or half of an Fv comprising only three CDRs specific for a target) can have the ability to recognize and bind target, although at a lower affinity than the entire binding site.

"Single-chain Fv" or "scFv" antibody binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for target binding.

"Single domain antibodies" are composed of a single $V_H$ or $V_L$ domains which exhibit sufficient affinity to PD-1. In a specific embodiment, the single domain antibody is a camelized antibody (See, e.g., Riechmann, 1999, Journal of Immunological Methods 231:25-38).

The anti-PD-1 antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (See, e.g., Wolfson, 2006, Chem. Biol. 13(10):1011-2).

The anti-PD-1 antibodies or binding fragments may be antibodies or fragments whose sequences have been modified to alter at least one constant region-mediated biological effector function. For example, in some embodiments, an anti-PD-1 antibody may be modified to reduce at least one constant region-mediated biological effector function relative to the unmodified antibody, e.g., reduced binding to one or more of the Fc receptors (FcγR) such as FcγRI, FcγRIIA, FcγRIIB, FcγRIIIA and/or FcγRIIIB. FcγR binding can be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reduction in FcγR binding ability of the antibody can also reduce other effector functions which rely on FcγR interactions, such as opsonization, phagocytosis and antigen-dependent cellular cytotoxicity ("ADCC").

The anti-PD-1 antibody or binding fragment described herein include antibodies that have been modified to acquire or improve at least one constant region-mediated biological effector function relative to an unmodified antibody, e.g., to enhance FcγR interactions (See, e.g., US Patent Appl. No. 2006/0134709). For example, an anti-PD-1 antibody of the disclosure can have a constant region that binds FcγRI, FcγRIIA, FcγRIIB, FcγRIIIA and/or FcγRIIIB with greater affinity than the corresponding wild type constant region.

Thus, antibodies of the disclosure may have alterations in biological activity that result in increased or decreased opsonization, phagocytosis, or ADCC. Such alterations are known in the art. For example, modifications in antibodies that reduce ADCC activity are described in U.S. Pat. No. 5,834,597. An exemplary ADCC lowering variant corresponds to "mutant 3" (also known as "M3," shown in FIG. 4 of U.S. Pat. No. 5,834,597) in which residues 234 and 237 (using EU numbering) are substituted with alanines. A mutant 3 (also known as "M3") variation may be used in a number of antibody isotypes, e.g., IgG$_2$.

Additional substitutions that can modify FcγR binding and/or ADCC effector function of an anti-PD-1 antibody include the K322A substitution or the L234A and L235A double substitution in the Fc region. See, e.g., Hezareh, et al. J. Virol., 75 (24): 12161-12168 (2001).

In some embodiments, the anti-PD-1 antibodies of the disclosure have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

The anti-PD-1 antibodies of the disclosure can comprise modified (or variant) CH2 domains or entire Fc domains that include amino acid substitutions that increase binding to FcγRIIB and/or reduced binding to FcγRIIIA as compared to the binding of a corresponding wild-type CH2 or Fc region. Variant CH2 or variant Fc domains have been described in U.S. Patent Appl. No. 2014/0377253. A variant CH2 or variant Fc domain typically includes one or more substitutions at position 263, position 266, position 273, and position 305, wherein the numbering of the residues in the Fc domain is that of the EU index as in Kabat. In some embodiments, the anti-PD-1 antibodies comprise one or more substitutions selected from V263L, V266L, V273C, V273E, V273F, V273L, V273M, V273S, V273Y, V305K, and V305W, relative to the wild-type CH2 domain. In specific embodiments, the one or more substitutions of the CH2 domain are selected from V263L, V273E, V273F, V273M, V273S, and V273Y, relative to the CH2 domain of a human IgG$_1$. For example, the one or more substitutions of an IgG$_1$ CH2 domain can be V273E. In another specific embodiment, the anti-PD-1 antibody of the disclosure comprises a variant IgG$_1$ hinge region comprising the amino acid substitution V263L.

Other examples of variant CH2 or variant Fc domains that can afford increased binding to FcγRIIB and/or reduced binding to FcγRIIIA as compared to the binding of a corresponding wild-type CH2 or Fc region include those found in Vonderheide, et al. Clin. Cancer Res., 19(5), 1035-1043 (2013), such as S267E or S267E/L328F in human IgG$_1$.

Anti-PD-1 antibodies or binding fragments that comprise a human IgG$_4$ constant region can comprise the S228P mutation, which has been reported to prevent Fab arm exchange. See, e.g., Silva, J P et al. Journal of Biological Chemistry, 290(9), 5462-5469 (2015).

In some embodiments, the anti-PD-1 antibodies or binding fragments include modifications that increase or decrease their binding affinities to the fetal Fc receptor, FcRn, for example, by mutating the immunoglobulin constant region segment at particular regions involved in FcRn interactions (see, e.g., WO 2005/123780). In particular embodiments, an anti-PD-1 antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. An exemplary substitution known to modify Fc effector function is the Fc substitution M428L, which can occur in combination with the Fc substitution T250Q. Additional specific combinations of suitable amino acid substitutions are identified in Table 1 of U.S. Pat. No. 7,217,797. Such mutations increase binding to FcRn, which protects the antibody from degradation and increases its half-life.

An anti-PD-1 antibody may have one or more amino acids inserted into one or more of its CDRs, for example as described in Jung and Plückthun, 1997, Protein Engineering 10:9, 959-966; Yazaki et al., 2004, Protein Eng. Des Sel. 17(5):481-9. Epub 2004 Aug. 17; and U.S. Pat. Appl. No. 2007/0280931.

Anti-PD-1 antibodies with high affinity for human PD-1 may be desirable for therapeutic and diagnostic uses. Accordingly, the present disclosure contemplates antibodies having a high binding affinity to human PD-1. In specific embodiments, the anti-PD-1 antibodies that bind human PD-1 with an affinity of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind human PD-1 with an affinity in the range of about 1 pM to about 100 nM, or an affinity ranging between any of the foregoing values.

Affinity of anti-PD-1 antibodies for human PD-1 can be determined using techniques well known in the art or described herein, such as for example, but not by way of limitation, ELISA, isothermal titration calorimetry (ITC), surface plasmon resonance, or fluorescent polarization assay.

Anti-PD-1 antibodies generally comprise a heavy chain comprising a variable region (V$_H$) having three complementarity determining regions ("CDRs") referred to herein (in N→C order) as V$_H$ CDR#1, V$_H$ CDR#2, and V$_H$ CDR#3, and a light chain comprising a variable region (V$_L$) having three complementarity determining regions referred to herein (in N→C order) as V$_L$ CDR#1, V$_L$ CDR#2, and V$_L$ CDR#3. The amino acid sequences of exemplary CDRs, as well as the amino acid sequence of the V$_H$ and V$_L$ regions of the heavy and light chains of exemplary anti-PD-1 are provided herein. Specific embodiments of anti-PD-1 antibodies include these exemplary CDRs and/or V$_H$ and/or V$_L$ sequences, as well as antibodies that compete for binding human PD-1 with such antibodies.

In some embodiments, an anti-PD-1 antibody is suitable for administration to humans. In a specific embodiment, the anti-PD-1 antibody is humanized. In some embodiments, amino acid sequences of the CDRs of an anti-PD-1 antibody are selected from the following sequences:

| CDR | Sequence (N→C) | Identifier |
|---|---|---|
| V$_H$ CDR#1: | GYTFTHYGMN | (SEQ ID NO: 11) |
| V$_H$ CDR#2: | WVNTYTGEPTYADDFKG | (SEQ ID NO: 12) |
| V$_H$ CDR#3: | EGEGLGFGD | (SEQ ID NO: 13) |
| | EGEGIGFGD | (SEQ ID NO: 21) |
| | EGEGVGFGD | (SEQ ID NO: 22) |
| | EGEGMGFGD | (SEQ ID NO: 23) |
| V$_L$ CDR#1: | RSSQSIVHSHGDTYLE | (SEQ ID NO: 14) |
| V$_L$ CDR#2: | KVSNRFS | (SEQ ID NO: 15) |
| V$_L$ CDR#3: | FQGSHIPVT | (SEQ ID NO: 16) |

Specific exemplary embodiments of anti-PD-1 antibodies with the above CDRs are described herein. In some embodiments, an anti-PD-1 antibody has the CDRs of SEQ ID NOS: 11, 12, 13, 14, 15, and 16. In some embodiments, an anti-PD-1 antibody has the CDRs of SEQ ID NOS: 11, 12, 21, 14, 15, and 16. In some embodiments, an anti-PD-1 antibody has the CDRs of SEQ ID NOS: 11, 12, 22, 14, 15, and 16. In some embodiments, an anti-PD-1 antibody has the CDRs of SEQ ID NOS: 11, 12, 23, 14, 15, and 16.

In some embodiments, each CDR of an anti-PD-1 antibody, independently of the others, is selected to correspond in sequence to the respective CDR of an antibody provided in TABLE 3. In some embodiments, an anti-PD-1 antibody is an IgG, and has a V$_H$ and V$_L$ corresponding in sequence to the V$_H$ and V$_L$ of an antibody provided in TABLE 3.

In some embodiments, an anti-PD-1 antibody comprises a V$_H$ chain corresponding in sequence to SEQ ID NO:31; and a V$_L$ chain corresponding in sequence to SEQ ID NO:41. In some embodiments, an anti-PD-1 antibody comprises a V$_H$ chain corresponding in sequence to SEQ ID NO:32; and a V$_L$ chain corresponding in sequence to SEQ ID NO:42. In some embodiments, an anti-PD-1 antibody comprises a V$_H$ chain corresponding in sequence to SEQ ID NO:33; and a V$_L$ chain corresponding in sequence to SEQ ID NO:42. In some embodiments, an anti-PD-1 antibody comprises a V$_H$ chain corresponding in sequence to SEQ ID NO:34; and a V$_L$ chain corresponding in sequence to SEQ ID NO:42. In some embodiments, an anti-PD-1 antibody comprises a V$_H$ chain corresponding in sequence to SEQ ID NO:35; and a V$_L$ chain corresponding in sequence to SEQ ID NO:42. In some embodiments, an anti-PD-1 antibody comprises a V$_H$ chain corresponding in sequence to SEQ ID NO:36; and a V$_L$ chain corresponding in sequence to SEQ ID NO:42.

Certain mutations of a V$_H$ or V$_L$ sequence in an anti-PD-1 antibody described herein would be understood by a person of skill to afford anti-PD-1 antibodies within the scope of the disclosure. Mutations may include amino acid substitutions, additions, or deletions from a V$_H$ or V$_L$ sequence as disclosed herein while retaining significant anti-PD-1 activity. Accordingly, in some embodiments, an anti-PD-1 antibody comprises a V$_H$ sequence having at least 85%, at least 90%, at least 93%, at least 95%, at least 96%, at least 97%, at least 98%, or at least 99% sequence identity to the V$_H$ sequence of any one of the antibodies shown in TABLE 3. An anti-PD-1 antibody can comprise a V$_H$ sequence having up to 8, up to 7, up to 6, up to 5, up to 4, up to 3, or up to 2 mutations compared with the V$_H$ sequence of any one of the antibodies shown in TABLE 3. In some embodiments, an anti-PD-1 antibody can comprise a V$_H$ sequence having 5 or fewer, 4 or fewer, 3 or fewer, or 2 or fewer mutations compared with the V$_H$ sequence of any one of the antibodies shown in TABLE 3. In some embodiments, an anti-PD-1 antibody comprises a V$_L$ sequence having at least 85%, at least 90%, at least 93%, at least 95%, at least 96%, at least 97%, at least 98%, or at least 99% sequence identity to the V$_L$ sequence of any one of the antibodies shown in TABLE 3. An anti-PD-1 antibody can comprise a V$_L$ sequence having up to 8, up to 7, up to 6, up to 5, up to 4, up to 3, or up to 2 mutations compared with the V$_L$ sequence of any one of the antibodies shown in TABLE 3. In some embodiments, an anti-PD-1 antibody can comprise a V$_L$ sequence having 5 or fewer, 4 or fewer, 3 or fewer, or 2 or fewer mutations compared with the V$_L$ sequence of any one of the antibodies shown in TABLE 3.

In some embodiments, an anti-PD-1 antibody comprises a heavy chain amino acid sequence according to:
EIQLVQSGAEVKKPGSSVKVSCKAS GYTFTHYGMNWVRQAPGQGLEWVG WVNTYTGEPTYADDFKGRLTFTLDTSTSTAYMELSS LRSEDTAVYYCTREGEGLGFGDWGQGTTVTVSSAST KGPSVFPLAPSSKSTSGGTAALGCLVKDYFPEPVT- VSWNSGALTSGVHTFPAVLQSSGLYSLSSVVTV PSSS- LGTQTYICNVNHKPSNTKVDKKVEPKSCDKTHTCPP- CPAPEAAGGPSVFLFPPKPKDTLMIS RTPEVTCVVVDVSHEDPEVKFNWYVDGVEVHNAK- TKPREEQYNSTYRVVSVLTVLHQDWLNGKEY KCK- VSNKALPAPIEKTISKAKGQPREPQVYTLPPSREEMT- KNQVSLTCLVKGFYPSDIAVEWESNG QPENNYKTTPPVLDSDGSFFLYSKLTVDKSRWQQGN- VFSCSVMHEALHNHYTQKSLSLSPGK (SEQ ID NO:51);
and a light chain amino acid sequence according to:
DVVMTQSPLSLPVTPGEPASISC RSSQSIVHSHGDTYLEWYLQKPGQSPQLLIY KVSNRFSGVP DRFSGSGSGTDFTLKISRVEAED- VGVYYC FQGSHIPVTFGQGTKLEIKRTVAAPSVFIFPPSDEQ LKSGTASVVCLLNNFYPREAKVQWKVDNALQSGN- SQESVTEQDSKDSTYSLSSTLTLSKADYEKHK VYACEVTHQGLSSPVTKSFNRGEC (SEQ ID NO:61),
wherein the underlined amino acids represent the CDRS and the italicized amino acids represent the constant regions.

Post-translational modifications to the sequences of an anti-PD-1 antibody may occur, such as cleavage of one or more (e.g., 1, 2, 3, or more) amino acid residues on the C-terminal end of the antibody heavy chain.

In some embodiments, an anti-PD-1 antibody comprises a heavy chain amino acid sequence according to:
EIQLVQSGAEVKKPGSSVKVSCKAS GYTFTHYGMNWVRQAPGQGLEWVG WVNTYTGEPTYADDFKGRLTFTLDTSTSTAYMELSS LRSEDTAVYYCTREGEGLGFGDWGQGTTVTVSSAST KGPSVFPLAPSSKSTSGGTAALGCLVKDYFPEPVT- VSWNSGALTSGVHTFPAVLQSSGLYSLSSVVTV PSSS- LGTQTYICNVNHKPSNTKVDKKVEPKSCDKTHTCPP- CPAPEAAGGPSVFLFPPKPKDTLMIS RTPEVTCVVVDVSHEDPEVKFNWYVDGVEVHNAK- TKPREEQYNSTYRVVSVLTVLHQDWLNGKEY KCK- VSNKALPAPIEKTISKAKGQPREPQVYTLPPSREEMT- KNQVSLTCLVKGFYPSDIAVEWESNG QPENNYKTTPPVLDSDGSFFLYSKLTVDKSRWQQGN- VFSCSVMHEALHNHYTQKSLSLSPG (SEQ ID NO:52);
and a light chain amino acid sequence according to:
DVVMTQSPLSLPVTPGEPASISC RSSQSIVHSHGDTYLEWYLQKPGQSPQLLIY KVSNRFSGVP DRFSGSGSGTDFTLKISRVEAED- VGVYYC FQGSHIPVTFGQGTKLEIKRTVAAPSVFIFPPSDEQ LKSGTASVVCLLNNFYPREAKVQWKVDNALQSGN- SQESVTEQDSKDSTYSLSSTLTLSKADYEKHK VYACEVTHQGLSSPVTKSFNRGEC (SEQ ID NO:61), wherein the underlined amino acids represent the CDRS and the italicized amino acids represent the constant regions.

Additional post-translational modifications of an anti-PD-1 antibody may include glycosylation. Common biantennary complexes can be composed of a core structure having two N-acetylglucosamine (GlcNAc), three mannose, and two GlcNAc residues that are β-1,2 linked to α-6 mannose and α-3 mannose to form two antennae. One or more fucose (Fuc), galactose (Gal), high mannose glycans Man-5 or Man-9, bisecting GlcNAc, and sialic acid including N-acetylneuraminic acid (NANA) or N-glycolylneuraminic acid (NGNA) residues may be attached to the core. N-linked glycoforms may include G0 (protein having a core biantennary glycosylation structure), G0F (fucosylated G0), G0F GlcNAc, G1 (protein having a core glycosylation structure with one galactose residue), G1F (fucosylated G1), G2 (protein having a core glycosylation structure with two galactose residues), and/or G2F (fucosylated G2). In some embodiments, an anti-PD-1 antibody has a G0F glycan.

In some embodiments, the anti-PD-1 antibodies compete for binding human PD-1 in in vitro assays with a reference antibody. In some embodiments, the anti-PD-1 antibodies compete for binding human PD-1 on cells expressing human PD-1. The reference antibody may be any of the anti-PD-1 antibodies described herein. In some embodiments, the reference antibody is an antibody provided in TABLE 3. In specific embodiments, the reference antibody is selected from mouse antibody 12A11 ("Mu12A11"). In some embodiments, the reference antibody is a humanized version of Mu12A11. In a specific embodiment, the reference antibody is humanized antibody 12A11.1b ("Hu12A11.1b") or humanized antibody 12A11.2b M99L ("Hu12A11.2b4").

In some embodiments, the anti-PD-1 antibodies antagonize, e.g., inhibit, human PD-1 (SEQ ID NO:1). PD-1 receptor antagonism can occur by a number of mechanisms, for example, by inhibiting binding of PD-1 by human PD-L1 (SEQ ID NO:3) or PD-L2 (SEQ ID NO:4).

The anti-PD-1 antibodies described herein generally bind specifically to human PD-1. Cross reactivity of the antibodies for binding to PD-1 from other species, for example, from monkey, e.g., cynomolgus monkey, may offer advantages, such as the ability to test in monkey animal models for biological activity. Such animal model testing may be used to screen anti-PD-1 antibodies to select properties related to efficacy, e.g., favorable pharmacokinetics, or those related to safety, e.g., decreased hepatic toxicity. In some embodiments, the anti-PD-1 antibodies bind to cynomolgus PD-1 as well as human PD-1.

Assays for competition include, but are not limited to, a radioactive material labeled immunoassay (RIA), an enzyme-linked immunosorbent assay (ELISA), a sandwich ELISA, fluorescence activated cell sorting (FACS) assays, and surface plasmon resonance assays.

In conducting an antibody competition assay between a reference antibody and a test antibody (irrespective of species or isotype), one may first label the reference with a detectable label, such as a fluorophore, biotin or an enzymatic (or even radioactive) label to enable subsequent identification. In this case, cells expressing human PD-1 are incubated with unlabeled test antibody, labeled reference antibody is added, and the intensity of the bound label is measured. If the test antibody competes with the labeled reference antibody by binding to an overlapping epitope, the intensity will be decreased relative to a control reaction carried out without test antibody.

In a specific embodiment of this assay, the concentration of labeled reference antibody that yields 80% of maximal binding ("$\text{conc}_{80\%}$") under the assay conditions (e.g., a specified density of cells) is first determined, and a competition assay carried out with 10× $\text{conc}_{80\%}$ of unlabeled test antibody and $\text{conc}_{80\%}$ of labeled reference antibody.

The inhibition can be expressed as an inhibition constant, or $K_i$, which is calculated according to the following formula:

$$K_i = IC_{50}/(1+[\text{reference } Ab \text{ concentration}]/K_d),$$

where $IC_{50}$ is the concentration of test antibody that yields a 50% reduction in binding of the reference antibody and $K_d$ is the dissociation constant of the reference antibody, a measure of its affinity for human PD-1. Antibodies that compete with anti-PD-1 antibodies disclosed herein can have a $K_i$ from 10 pM to 10 nM under assay conditions described herein.

In various embodiments, a test antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

A specific assay and assay conditions useful for assessing whether an antibody competes for binding human PD-1 with a reference antibody as described herein is provided in Section 8.1.5.

7.4. Polynucleotides Encoding the Anti-PD-1 Antibodies, Expression Systems and Methods of Making the Antibodies The present disclosure encompasses nucleic acid molecules encoding immunoglobulin light and heavy chain genes for anti-PD-1 antibodies, vectors comprising such nucleic acids, and host cells capable of producing the anti-PD-1 antibodies of the disclosure.

An anti-PD-1 antibody of the disclosure can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

To generate nucleic acids encoding such anti-PD-1 antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat, E. A. et al., 1991, Sequences of Proteins of Immunological Interest, Fifth Edition, U.S. Department of Health and Human Services, NIH Publication No. 91-3242; Tomlinson et al., 1992, J. Mol. Biol. 22T:116-198; and Cox et al., 1994, Eur. J. Immunol. 24:827-836; the contents of each of which are incorporated herein by reference).

Once DNA fragments encoding anti-PD-1 antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2, CH3 and, optionally, CH4). The sequences of human heavy chain constant region genes are known in the art (See, e.g., Kabat, E. A., et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat, et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence $(Gly_4\sim Ser)_3$ (SEQ ID NO:5), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-PD-1 antibodies of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-PD-1 antibody-related light or heavy chain sequences, the expression vector can already carry antibody constant region sequences. For example, one approach to converting the anti-PD-1 monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968, 615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the antibodies of the disclosure in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-PD-1 antibody of this disclosure.

Recombinant DNA technology can also be used to remove some or all of the DNA encoding either or both of the light and heavy chains that is not necessary for binding to human PD-1. The molecules expressed from such truncated DNA molecules are also encompassed by the antibodies of the disclosure.

For recombinant expression of an anti-PD-1 antibody of the disclosure, the host cell can be co-transfected with two expression vectors of the disclosure, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-PD-1 antibody has been obtained, further alterations or mutations can be introduced into the coding sequence, for example to generate nucleic acids encoding antibodies with different CDR sequences, antibodies with reduced affinity to the Fc receptor, or antibodies of different subclasses.

The anti-PD-1 antibodies of the disclosure can also be produced by chemical synthesis (e.g., by the methods described in Solid Phase Peptide Synthesis, 2$^{nd}$ ed., 1984 The Pierce Chemical Co., Rockford, Ill.). Variant antibodies can also be generated using a cell-free platform (See, e.g., Chu et al., Biochemia No. 2, 2001 (Roche Molecular Biologicals) and Murray et al., 2013, Current Opinion in Chemical Biology, 17:420-426).

Once an anti-PD-1 antibody of the disclosure has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-PD-1 antibodies of the present disclosure can be fused to heterologous polypeptide sequences described herein or otherwise known in the art to facilitate purification.

Once isolated, the anti-PD-1 antibody can, if desired, be further purified, e.g., by high performance liquid chromatography (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

7.5. Pharmaceutical Compositions

The anti-PD-1 antibodies described herein may be in the form of compositions comprising the antibody and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an anti-PD-1 antibody described herein per dose. The quantity of anti-PD-1 antibody included in a unit dose will depend on the disease being treated, as well as other factors as are well known in the art. Such unit dosages may be in the form of a lyophilized dry powder containing an amount of antibody suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of the anti-PD-1 antibody suitable for a single administration.

The pharmaceutical compositions may also be supplied in bulk form containing quantities of anti-PD-1 antibody suitable for multiple administrations.

Pharmaceutical compositions may be prepared for storage as lyophilized formulations or aqueous solutions by mixing an antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives should be nontoxic to the recipients at the dosages and concentrations employed.

Buffering agents help to maintain the pH in the range which approximates physiological conditions. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), phosphate buffers (e.g., phosphoric acid-monosodium phosphate mixture, phosphoric acid-disodium phosphate mixture, monosodium phosphate-disodium phosphate mixture, etc.), gluconate buffers (e.g., gluconic acid-sodium gluconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, fumarate buffers, histidine buffers and trimethylamine salts such as 2-amino-2-hydroxymethyl-propane-1,3-diol (i.e., Tris, THAM, or tris(hydroxymethyl)aminomethane) can be used.

Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, leucine, 2-phenylalanine, glutamic acid, threonine, etc., organic sugars or sugar alcohols, such as lactose, trehalose, stachyose, mannitol, sorbitol, xylitol, ribitol, myoinositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thiosulfate; low molecular weight polypeptides (e.g., peptides of 10 residues or fewer); hydrophilic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 weight % per weight of anti-PD-1 antibody.

Non-ionic surfactants or detergents (also known as "wetting agents") may be added to help solubilize the glycoprotein as well as to protect the glycoprotein against agitation-induced aggregation, which also permits the formulation to be exposed to shear surface stressed without causing denaturation of the protein. Suitable non-ionic surfactants include polysorbates (20, 80, etc.), poloxamers (184, 188 etc.), and pluronic polyols. Non-ionic surfactants may be present in a range of about 0.05 mg/mL to about 1.0 mg/mL.

A specific exemplary embodiment of an aqueous composition suitable for administration via intravenous infusion comprises 20 mg/mL of an anti-PD-1 antibody comprising a heavy chain sequence of SEQ ID NO:51 or SEQ ID NO:52, and a light chain sequence of SEQ ID NO:61, 15 mM histidine pH 5.7, 8.0% (w/v) sucrose, and 0.05% (w/v) polysorbate 80. The composition may be in the form of a lyophilized powder that, upon reconstitution with sterile water or other solution suitable for injection or infusion (for example, 0.9% saline, Ringer's solution, lactated Ringer's solution, etc.) provides the above aqueous composition. The composition, or other embodiments of compositions, may also be in the form of a syringe or other device suitable for injection and/or infusion pre-filled with a quantity of composition suitable for a single administration of the anti-PD-1 antibody.

7.6. Methods of Use

7.6.1. Therapeutic Benefit

Data provided herein demonstrate that the disclosed anti-PD-1 antibodies antagonize PD-1 in the presence of cancer cells and exert potent anticancer activity against cancers such as solid tumors and blood malignancies in vivo. Accordingly, the anti-PD-1 antibodies, binding fragments, and/or pharmaceutical compositions comprising the anti-PD-1 antibodies may be used therapeutically to treat solid tumors or blood malignancies.

In some embodiments, the method involves administering to a human patient having a solid tumor an amount of an anti-PD-1 antibody that antagonizes PD-1, and kills tumor cells at a rate effective to provide therapeutic benefit. Solid tumors that may be treated with the anti-PD-1 antibody include, but are not limited to, adrenal cancers, bladder cancers, bone cancers, brain cancers, breast cancers (e.g., triple negative breast cancer), cervical cancers, colorectal cancers, endometrial cancers, esophageal cancers, eye cancers, gastric cancers, head and neck cancers, kidney cancers (e.g., advanced renal cell carcinoma), liver cancers (e.g., hepatocellular carcinoma, cholangiocarcinoma), lung cancers (e.g., non-small cell lung cancer, mesothelioma, small cell lung cancer), head and neck cancers, melanomas (e.g., unresectable or metastatic melanoma, advanced malignant melanoma), oral cancers, ovarian cancers, penile cancers, prostate cancers, pancreatic cancers, skin cancers (e.g., Merkel cell carcinoma), testicular cancers, thyroid cancers, uterine cancers, vaginal cancers, and tumors with evidence of DNA mismatch repair deficiency. The cancers may be comprised of tumor cells that express PD-L1 or PD-L2, cancers comprised of tumor cells that do not express PD-L1 or PD-L2, or cancers comprised of tumor cells, some of which express PD-L1 or PD-L2 and some of which do not. The cancer may be newly diagnosed and naïve to treatment, or may be relapsed, refractory, or relapsed and refractory, or a metastatic form of a solid tumor. In some embodiments, the solid tumor is selected from bladder cancer, breast cancer, head and neck cancer, kidney cancer, lung cancer, lymphoma, melanoma, and gastric cancer. In some embodiments, the solid tumor is selected from: melanoma (e.g., unresectable or metastatic melanoma), lung cancer (e.g., non-small cell lung cancer), and renal cell carcinoma (e.g., advanced renal cell carcinoma). In some embodiments, the solid tumor is selected from triple negative breast cancer, ovarian cancer, hepatocellular carcinoma, gastric cancer, small cell lung cancer, mesothelioma, cholangiocarcinoma, Merkel cell carcinoma and tumors with evidence of DNA mismatch repair deficiency. In certain embodiments, the melanoma is BRAF V600 wild-type unresectable or metastatic melanoma. In other certain embodiments, the melanoma is BRAF V600 mutation-positive unresectable or metastatic melanoma. In certain embodiments, the lung cancer is metastatic non-small cell lung cancer with progression on or after platinum-based chemotherapy. In certain embodiments, the lung cancer is locally advanced or metastatic non-small cell lung cancer that has failed platinum-based therapy and is naïve to a PD-1 targeting agent. In certain embodiments, the head and neck cancer is metastatic (disseminated) head and neck squamous cell carcinoma of the oral cavity, oropharynx, hypopharynx, and larynx that is considered incurable by local therapies. In certain embodiments, the renal cell carcinoma is advanced renal cell carcinoma that has received prior anti-angiogenic therapy.

In some embodiments, the method of the disclosure involves administering to a human patient having a blood malignancy an amount of an anti-PD-1 antibody that antagonizes PD-1, and kills malignant cells at a rate effective to provide therapeutic benefit. The cancers may be comprised of malignant cells that express PD-L1 or PD-L2, cancers comprised of malignant cells that do not express PD-L1 or PD-L2, or cancers comprised of malignant cells, some of which express PD-L1 or PD-L2 and some of which do not. The cancer may be newly diagnosed and naïve to treatment, or may be relapsed, refractory, or relapsed and refractory, or a metastatic form of a blood malignancy. Blood-borne malignancies that may be treated with the anti-PD-1 antibody include, but are not limited to, myelomas (e.g., multiple myeloma), lymphomas (e.g., Hodgkin's lymphoma, non-Hodgkin's lymphoma, Waldenström's macroglobulinemia, mantle cell lymphoma), leukemias (e.g., chronic lymphocytic leukemia, acute myeloid leukemia, acute lymphocytic leukemia), and myelodysplastic syndromes.

As discussed above, the presently disclosed anti-PD-1 antibodies modulate an immunological response. Accordingly, patients having compromised immune systems may be excluded from treatment. In some embodiments, a patient is excluded after meeting one or more of the following criteria: (1) Active or prior documented autoimmune disease (including, but not limited to, inflammatory bowel disease, celiac disease, Wegener syndrome) within the past 2 years. (Subjects with childhood atopy or asthma, vitiligo, alopecia, Hashimoto syndrome, Grave's disease, or psoriasis not requiring systemic treatment (within the past 2 years) are not excluded); (2) History of primary immunodeficiency, bone marrow transplantation, chronic lymphocytic leukemia, solid organ transplantation, or previous clinical diagnosis of tuberculosis; (3) History of a coagulopathy or a platelet disorder; (4) Confirmed positive test results for human immunodeficiency virus (HIV), or subjects with chronic or active hepatitis B or C. (Subjects who have a history of hepatitis B or C who have documented cures after anti-viral therapy may be enrolled); (5) Prior grade ≥3 immune-mediated neurotoxicity or pneumonitis while receiving immunotherapy (including but not limited to agents directed against CTLA-4, PD-L1, or PD-1). In addition, any other prior grade ≥3 immune-mediated adverse event while receiving immunotherapy that has not resolved or become asymptomatic within 3 months; (6) Receipt of live, attenuated vaccine within 28 days prior to the first dose of the anti-PD-1 antibody.

An anti-PD-1 antibody of the disclosure may be administered alone (monotherapy) or adjunctive to, or with, other anti-cancer therapies and/or targeted or non-targeted anti-cancer agents. When administered as an anti-PD-1 monotherapy, one or more antibodies may be used. Whether administered as monotherapy or adjunctive to, or with, other therapies or agents, an amount of anti-PD-1 antibody is administered such that the overall treatment regimen provides therapeutic benefit.

By therapeutic benefit is meant that the use of anti-PD-1 antibodies to treat cancer in a patient results in any demonstrated clinical benefit compared with no therapy (when appropriate) or to a known standard of care. Clinical benefit can be assessed by any method known to one of ordinary skill in the art. In one embodiment, clinical benefit is assessed based on objective response rate (ORR) (determined using RECIST version 1.1), duration of response (DOR), progression-free survival (PFS), and/or overall survival (OS). In some embodiments, a complete response indicates therapeutic benefit. In some embodiments, a partial response indicates therapeutic benefit. In some embodiments, stable disease indicates therapeutic benefit. In some embodiments, an increase in overall survival indicates therapeutic benefit. In some embodiments, therapeutic benefit may constitute an improvement in time to disease progression and/or an improvement in symptoms or quality of life. In other embodiments, therapeutic benefit may not translate to an increased period of disease control, but rather a markedly reduced symptom burden resulting in improved quality of life. As will be apparent to those of skill in the art, a therapeutic benefit may be observed using the anti-PD-1 antibodies alone (monotherapy) or adjunctive to, or with, other anti-cancer therapies and/or targeted or non-targeted anti-cancer agents.

Typically, therapeutic benefit is assessed using standard clinical tests designed to measure the response to a new treatment for cancer. To assess the therapeutic benefits of the anti-PD-1 antibodies described herein one or a combination of the following tests can be used: (1) the Response Evaluation Criteria In Solid Tumors (RECIST) version 1.1, (2) immune-related RECIST (irRECIST), (3) the Eastern Cooperative Oncology Group (ECOG) Performance Status, (4) immune-related response criteria (irRC), (5) disease evaluable by assessment of tumor antigens, (6) validated patient reported outcome scales, and/or (7) Kaplan-Meier estimates for overall survival and progression free survival.

Assessment of the change in tumor burden is an important feature of the clinical evaluation of cancer therapeutics. Both tumor shrinkage (objective response) and time to the development of disease progression are important endpoints in cancer clinical trials. Standardized response criteria, known as RECIST (Response Evaluation Criteria in Solid Tumors), were published in 2000. An update (RECIST 1.1) was released in 2009. RECIST criteria are typically used in clinical trials where objective response is the primary study endpoint, as well as in trials where assessment of stable disease, tumor progression or time to progression analyses are undertaken because these outcome measures are based on an assessment of anatomical tumor burden and its change over the course of the trial. TABLE 4 provides the definitions of the response criteria used to determine objective tumor response to a study drug, such as the anti-PD-1 antibodies described herein.

TABLE 4

| Response | Criteria |
|---|---|
| Complete Response (CR) | Disappearance of all target lesions. Any pathological lymph nodes (whether target or non-target) must have reduction in short axis to <10 mm. |

TABLE 4-continued

| Response | Criteria |
| --- | --- |
| Partial Response (PR) | At least a 30% decrease in the sum of diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) | Neither sufficient shrinkage to qualify for PR nor sufficient increase to qualify for PD, taking as reference the smallest sum diameters while on study. |

Secondary outcome measures that can be used to determine the therapeutic benefit of the anti-PD-1 antibodies described herein include, Objective Response Rate (ORR), Progression Free Survival (PFS), Overall Survival (OS), Duration of Overall Response (DOR), and Depth of Response (DpR). ORR is defined as the proportion of the participants who achieve a complete response (CR) or partial response (PR). PFS is defined as the time from the first dose date of an anti-PD-1 antibody to either disease progression or death, whichever occurs first. OS is defined as the length of time from either the date of diagnosis or the start of treatment for a disease, that patients diagnosed with the disease are still alive. DOR is defined as the time from the participant's initial CR or PR to the time of disease progression. DpR is defined as the percentage of tumor shrinkage observed at the maximal response point compared to baseline tumor load. Clinical endpoints for both ORR and PFS can be determined based on RECIST 1.1 criteria described above.

Additional criteria that may be used for clinical evaluation specific to cancer patients undergoing immune therapy treatment include the standardized immune-related RECIST (ir-RECIST) criteria. See, e.g., Nishino, M. et al. *Eur. J. Radiol.*, 84(7), pages 1259-1268 (2015 July). These guidelines modified the RECIST 1.1 criteria above with consideration of potential immunomodulatory effects. TABLE 5 provides the definitions of the response criteria used to determine objective tumor response to an immunomodulatory drug, such as the anti-PD-1 antibodies described herein.

TABLE 5

| Response | Criteria |
| --- | --- |
| Complete Response (irCR) | Complete disappearance of all measurable and non-measurable lesions. Lymph nodes must decrease to < 10 mm in short axis. |
| Partial Response (irPR) | Decrease of ≥ 30% in total measured tumor burden relative to baseline, non-target lesions are irNN, and no unequivocal progression of new non-measurable lesions |
| Progressive Disease (irPD) | At least a 20% increase and at least 5 mm absolute increase in TMTB compared to nadir, or irPD for non-target or new non-measurable lesions. Confirmation of progression is recommended at least 4 weeks after the first irPD assessment. |
| Non-irCR or non-irPD (irNN) | No target disease was identified at baseline and at follow-up the patient fails to meet criteria for irCR or irPD |
| Stable Disease (irSD) | Neither sufficient shrinkage to qualify for irPR nor sufficient increase to qualify for irPD, taking as reference the smallest sum diameters while on study. |
| irNE | Used in exceptional cases where insufficient data exists. |

The ECOG Scale of Performance Status shown in TABLE 6 is used to describe a patient's level of functioning in terms of their ability to care for themselves, daily activity, and physical ability. The scale was developed by the Eastern Cooperative Oncology Group (ECOG), now part of the ECOG-ACRIN Cancer Research Group, and published in 1982.

TABLE 6

| Grade | ECOG Performance Status |
| --- | --- |
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

Another set of criteria that can be used to characterize fully and to determine response to immunotherapeutic agents, such as antibody-based cancer therapies, is the immune-related response criteria (irRC), which was developed for measurement of solid tumors in 2009, and updated in 2013 (Wolchok, et al. Clin. Cancer Res. 2009; 15(23): 7412-7420 and Nishino, et al. Clin. Cancer Res. 2013; 19(14): 3936-3943). The updated irRC criteria are typically used to assess the effect of an immunotherapeutic agent, such as an anti-PD-1 antibody described herein, on tumor burden, and defines response according to TABLE 7.

TABLE 7

| Response | Criteria |
| --- | --- |
| Complete Response (CR) | Disappearance of all target lesions in two consecutive observations not less than 4 weeks apart |
| Partial Response (PR) | At least a 30% decrease in the sum of the longest diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). (Note: the appearance of one or more new lesions is not considered progression. The measurement of new lesions is included in the sum of the measurements). |
| Stable Disease (SD) | Neither sufficient shrinkage to qualify for PR nor sufficient increase to qualify for PD, taking as reference the smallest sum diameters while on study. |

Tumor antigens that can be used to evaluate the therapeutic benefit of the anti-PD-1 antibodies described herein include ApoE, CD11c, CD40, CD45 (PTPRC), CD49D (ITGA4), CD80, CSF1R, CTSD, GZMB, Ly86, MS4A7, PIK3AP1, PIK3CD, CD74, CCL5, CCR5, CXCL10, IFNG, IL10RA1, IL-6, ACTA2, COL7A1, LOX, LRRC15, MCPT8, MMP10, NOG, SERPINE1, STAT1, TGFBR1, CTSS, PGF, VEGFA, C1QA, C1QB, ANGPTL4, EGLN, ANGPTL4, EGLN3, BNIP3, AIF1, CCL5, CXCL10, CXCL11, IFI6, PLOD2, KISS1R, STC2, DDIT4, OX40, OX40L, PFKFB3, PGK1, PDK1, AKR1C1, AKR1C2, CADM1, CDH11, COL6A3, CTGF, HMOX1, KRT33A, LUM, WNT5A, IGFBP3, MMP14, CDCP1, PDGFRA, TCF4, TGF, TGFB1, TGFB2, CD11b, ADGRE1 (EMR1, F4/80), CD86, CD68, MHC-Class II, CD3, HLA-DR, CD4, CD3, CD5, CD19, CD7, CD8, CD16, TCRαβ, TCRγδ, PD-1, PD-L1, CTLA-4, acid phosphatase, ACTH, alkaline phosphatase, alpha-fetoprotein CA-125, CA15-3, CA19-9, CA-195, C-212, CA-549, calcitonin, catecholamines, cathepsin-D, CEA, ERBB2 (HER2/neu), chromagranin-A, c-Myc, EGFR, ERA (estrogen receptor assay), ferritin, gastrin, 5-HIAA, hCG, alpha-HCG, beta-HCG, HVA, LDH1-5, NSE (neuron specific enolase), pancreatic polypeptide, PLAP, PLP, PRA (progesterone receptor A), proinsulin C-peptide, PSA, SMA, SCC, thyroglobulin, TDT, TPA, and alpha-TSH. These tumor antigens can be assessed at the DNA, RNA or protein level using DNA sequencing techniques, RNA sequencing techniques, gene chip microarray, PCR based methods, flow cytometry or immunohistochemistry methods as known to experts in the art.

One exemplary therapeutic benefit resulting from the use of anti-PD-1 antibodies described herein to treat solid tumors, whether administered as monotherapy or adjunctive to, or with, other therapies or agents, is a complete response. Another exemplary therapeutic benefit resulting from the use of anti-PD-1 antibodies described herein to treat solid tumors, whether administered as monotherapy or adjunctive to, or with, other therapies or agents, is a partial response.

Validated patient reported outcome scales can also be used to denote response provided by each patient through a specific reporting system. Rather than being disease focused, such outcome scales are concerned with retained function while managing a chronic condition. One non-limiting example of a validated patient reported outcome scale is PROMIS® (Patient Reported Outcomes Measurement Information System) from the United States National Institutes of Health. For example, PROMIS® Physical Function Instrument for adult cancer patients can evaluate self-reported capabilities for the functioning of upper extremities (e.g., dexterity), lower extremities (e.g., walking or mobility), and central regions (e.g., neck, back mobility), and includes routine daily activities, such as running errands.

Kaplan-Meier curves (Kaplan and Meier, J. Am. Stat. Assoc. 1958; 53(282): 457-481) can also be used to estimate overall survival and progression free survival for cancer patients undergoing anti-PD-1 antibody therapy in comparison to standard of care.

7.6.2. Adjunctive Therapies

The anti-PD-1 antibodies may be used adjunctive to, or with, other agents or treatments having anti-cancer properties. When used adjunctively, the anti-PD-1 antibody and other agent(s) may be formulated together in a single, combination pharmaceutical formulation, or may be formulated and administered separately, either on a single coordinated dosing regimen or on different dosing regimens. Agents administered adjunctive to or with the anti-PD-1 antibodies will typically have complementary activities to the anti-PD-1 antibodies such that the antibodies and other agents do not adversely affect each other.

Agents that may be used adjunctively with anti-PD-1 antibodies include, but are not limited to, alkylating agents, angiogenesis inhibitors, antibodies, antimetabolites, antimitotics, antiproliferatives, antivirals, aurora kinase inhibitors, apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, Bruton's tyrosine kinase (BTK) inhibitors, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, as well as combinations of one or more of these agents.

BiTE antibodies are bispecific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include, but are not limited to, altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, and trofosfamide.

Angiogenesis inhibitors include, but are not limited to, endothelial-specific receptor tyrosine kinase (Tie-2) inhibitors, epidermal growth factor receptor (EGFR) inhibitors, vascular endothelial growth factor receptor (VEGF) inhibitors, delta-like ligand 4 (DLL4) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, and vascular endothelial growth factor receptor tyrosine kinase (VEGFR) inhibitors.

Antibody drug conjugates include, but are not limited to, those that target c-Met kinase (e.g., ADCs described in U.S. Pat. No. 7,615,529), LRRC15, CD30 (e.g., ADCETRIS® (brentuximab vedotin)), CS1 (e.g., ADCs described in US publication no. 20160122430), DLL3 (e.g., rovalpituzumab tesirine (ROVA-T)), HER2 (e.g., KADCYLA® (trastuzumab emtansine)), EGFR (e.g., ADCs described in US publication no. 20150337042), and prolactin receptor (e.g., ADCs described in US publication no. 20140227294).

Antimetabolites include, but are not limited to, ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, ribavirin, triapine, trimetrexate, S-1, tiazofurin, tegafur, TS-1, vidarabine, and UFT.

Antivirals include, but are not limited to, ritonavir, acyclovir, cidofovir, ganciclovir, foscarnet, zidovudine, ribavirin, and hydroxychloroquine.

Aurora kinase inhibitors include, but are not limited to, ABT-348, AZD-1152, MLN-8054, VX-680, Aurora A-specific kinase inhibitors, Aurora B-specific kinase inhibitors and pan-Aurora kinase inhibitors.

Bcl-2 protein inhibitors include, but are not limited to, ABT-263 (navitoclax), AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl) amino)-3-nitrobenzene sulfonamide, N-(4-(4-((2-(4-chlorophenyl)-5,5-dimethyl-1-cyclohex-1-en-1-yl)methyl) piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, venetoclax and GX-070 (obatoclax).

Bcr-Abl kinase inhibitors include, but are not limited to, DASATINIB® (BMS-354825) and GLEEVEC® (imatinib).

BTK inhibitors include, but are not limited to, ibrutinib and acalabrutinib.

CDK inhibitors include, but are not limited to, AZD-5438, BMI-1040, BMS-032, BMS-387, CVT-2584, flavopyridol, GPC-286199, MCS-5A, PD0332991, PHA-690509, seliciclib (CYC-202, R-roscovitine), and ZK-304709.

COX-2 inhibitors include, but are not limited to, ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, and VIOXX® (rofecoxib).

EGFR inhibitors include, but are not limited to, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TAGRISSO® (osimertinib), TP-38, EGFR fusion protein, and TYKERB® (lapatinib).

ErbB2 receptor inhibitors include, but are not limited to, CP-724-714, CI-1033 (canertinib), HERCEPTIN® (trastuzumab), TYKERB® (lapatinib), OMNITARG® (2C4, pertuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, and mAB 2B-1.

Histone deacetylase inhibitors include, but are not limited to, depsipeptide, LAQ-824, MS-275, trapoxin, suberoylanilide hydroxamic acid (SAHA), TSA, and valproic acid.

HSP-90 inhibitors include, but are not limited to, 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090, and VER49009.

Inhibitors of apoptosis proteins include, but are not limited to, HGS1029, GDC-0145, GDC-0152, LCL-161, and LBW-242.

Activators of death receptor pathway include, but are not limited to, TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include, but are not limited to, Eg5 inhibitors such as AZD4877, ARRY-520; and CENPE inhibitors such as GSK923295A.

JAK-2 inhibitors include, but are not limited to, CEP-701 (lesaurtinib), XL019 and INCB018424.

MEK inhibitors include, but are not limited to, ARRY-142886, ARRY-438162, PD-325901, and PD-98059.

mTOR inhibitors include, but are not limited to, AP-23573, CCI-779, everolimus, RAD-001, rapamycin, temsirolimus, ATP-competitive TORC1/TORC2 inhibitors, including PI-103, PP242, PP30, and Torin 1.

Non-steroidal anti-inflammatory drugs include, but are not limited to, AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), and DAYPRO® (oxaprozin).

PDGFR inhibitors include, but are not limited to, C-451, CP-673 and CP-868596.

Platinum chemotherapeutics include, but are not limited to, cisplatin, ELOXATIN® (oxaliplatin) eptaplatin, lobaplatin, nedaplatin, PARAPLATIN® (carboplatin), satraplatin, and picoplatin.

Polo-like kinase inhibitors include, but are not limited to, BI-2536.

Phosphoinositide-3 kinase (PI3K) inhibitors include, but are not limited to, wortmannin, LY294002, XL-147, CAL-120, ONC-21, AEZS-127, ETP-45658, PX-866, GDC-0941, BGT226, BEZ235, and XL765.

Thrombospondin analogs include, but are not limited to, ABT-510, ABT-567, ABT-898, and TSP-1.

VEGFR inhibitors include, but are not limited to, ABT-869, AEE-788, ANGIOZYME™ (a ribozyme that inhibits angiogenesis (Ribozyme Pharmaceuticals (Boulder, Colo.) and Chiron (Emeryville, Calif.)), axitinib (AG-13736), AZD-2171, CP-547,632, CYRAMZA® (ramucirumab), IM-862, MACUGEN® (pegaptamib), NEXAVAR® (sorafenib, BAY43-9006), pazopanib (GW-786034), vatalanib (PTK-787, ZK-222584), SUTENT® (sunitinib, SU-11248), STIVARGA® (regorafenib), VEGF trap, and ZACTIMA™ (vandetanib, ZD-6474).

Antibiotics include, but are not limited to, intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), and zinostatin.

Topoisomerase inhibitors include, but are not limited to, aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, Onivyde™ (liposomal irinotecan), orathecin, pirarbucin, pixantrone, rubitecan, sobuzoxane, SN-38, tafluposide, and topotecan.

Antibodies include, but are not limited to, AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, OX-40 specific antibodies, PANOREX® (edrecolomab), RENCAREX® (WX G250), RITUXAN® (rituximab), ticilimumab, trastuzumab, pertuzumab, VECTIBIX® (panitumumab) and CD20 antibodies types I and II.

Hormonal therapies include, but are not limited to, ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), and ZOLADEX® (fosrelin, goserelin).

Deltoids and retinoids include, but are not limited to, seocalcitol (EB1089, CB1093), lexacalcitrol (KH1060), fenretinide, PANRETIN® (aliretinoin), ATRAGEN® (liposomal tretinoin), TARGRETIN® (bexarotene), and LGD-1550.

PARP inhibitors include, but are not limited to, ABT-888 (veliparib), KU-59436, AZD-2281 (olaparib), AG-014699 (rucaparib), MK4827 (niraparib), BMN-673 (talazoparib), iniparib, BSI-201, BGP-15, INO-1001, and ONO-2231.

Plant alkaloids include, but are not limited to, vincristine, vinblastine, vindesine, and vinorelbine.

Proteasome inhibitors include, but are not limited to, VELCADE® (bortezomib), KYPROLIS® (carfilzomib), MG132, NPI-0052, and PR-171.

Examples of immunologicals include, but are not limited to, interferons, immune checkpoint inhibitors, co-stimulatory agents, and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Immune check point inhibitors include antibodies that target PD-L1 (e.g., durvalumab, atezolizumab, avelumab, MEDI4736, MSB0010718C and MPDL3280A), and CTLA4 (cytotoxic lymphocyte antigen 4; e.g., ipilimumab, tremelimumab). Co-stimulatory agents include, but are not limited to, antibodies against CD3, CD40, CD40L, CD27, CD28, CSF1R, CD137 (e.g., urelumab), B7H1, GITR, ICOS, CD80, CD86, OX40, OX40L, CD70, HLA-DR, LIGHT, LIGHT-R, TIM3, A2AR, NKG2A, KIR (e.g., lirilumab), TGF-β (e.g., fresolimumab) and combinations thereof.

Other agents include, but are not limited to, ALFAFERONE® (IFN-α), BAM-002 (oxidized glutathione), BEROMUN® (tasonermin), BEXXAR® (tositumomab), CAMPATH® (alemtuzumab), dacarbazine, denileukin, epratuzumab, GRANOCYTE® (lenograstim), lentinan, leukocyte alpha interferon, imiquimod, melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZINBRYTA® (daclizumab high-yield process), and ZEVALIN® ($^{90}$Y-Ibritumomab tiuxetan).

Biological response modifiers are agents that modify defense mechanisms of living organisms or biological responses, such as survival, growth or differentiation of tissue cells to direct them to have anti-tumor activity and include, but are not limited to, krestin, lentinan, sizofiran, picibanil PF-3512676 (CpG-8954), and ubenimex.

Pyrimidine analogs include, but are not limited to, cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), and TROXATYL™ (triacetyluridine troxacitabine).

Purine analogs include, but are not limited to, LANVIS® (thioguanine) and PURINETHOL® (mercaptopurine).

Antimitotic agents include, but are not limited to, batabulin, epothilone D (KOS-862), N-(2-((4-hydroxyphenyl)amino)pyridin-3-yl)-4-methoxybenzenesulfonamide, ixabepilone (BMS 247550), TAXOL® (paclitaxel), TAXOTERE® (docetaxel), PNU100940 (109881), patupilone, XRP-9881 (larotaxel), vinflunine, and ZK-EPO (synthetic epothilone).

Ubiquitin ligase inhibitors include, but are not limited to, MDM2 inhibitors, such as nutlins, and NEDD8 inhibitors such as MLN4924.

Anti-PD-1 antibodies may also be used to enhance the efficacy of radiation therapy. Examples of radiation therapy include external beam radiation therapy, internal radiation therapy (i.e., brachytherapy) and systemic radiation therapy.

Anti-PD-1 antibodies may be administered adjunctive to or with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histrelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), and zorubicin, as well as combinations of any of these agents.

In some embodiments, an anti-PD-1 antibody is administered adjunctive to or with an antibody-drug conjugate targeting c-Met kinase for treating non-small cell lung cancer, head and neck cancer, pancreatic cancer, colorectal cancer, or gastric cancer.

In some embodiments, an anti-PD-1 antibody is administered adjunctive to or with an antibody-drug conjugate targeting LRRC15 for treating non-small cell lung cancer, head and neck cancer, pancreatic cancer, sarcoma, triple negative breast cancer, or melanoma.

In some embodiments, an anti-PD-1 antibody is administered adjunctive to or with an antibody-drug conjugate targeting EGFR for treating glioblastoma.

In some embodiments, an anti-PD-1 antibody is administered adjunctive to or with an antibody-drug conjugate targeting CS1 for treating a blood malignancy such as multiple myeloma.

In some embodiments, an anti-PD-1 antibody is administered adjunctive to or with an antibody-drug conjugate targeting DLL3 for treating small cell lung cancer or glioblastoma.

In some embodiments, an anti-PD-1 antibody is administered adjunctive to or with an anti-CD40 protein for treating head and neck cancer, lung cancer (such as adenocarcinoma, non-small cell lung cancer, mesothelioma, small cell lung cancer), melanoma, ovarian cancer or pancreatic cancer.

In some embodiments, an anti-PD-1 antibody is administered adjunctive to or with venetoclax for treating a blood malignancy such as chronic lymphocytic leukemia.

In some embodiments, an anti-PD-1 antibody is administered adjunctive to or with ibrutinib for treating a blood malignancy, such as chronic lymphocytic leukemia, mantle cell lymphoma, or Waldenström's macroglobulinemia, or a solid tumor.

In some embodiments, an anti-PD-1 antibody is administered adjunctive to or with ipilimumab and an antibody-drug conjugate targeting c-Met kinase for treating non-small cell lung cancer.

In some embodiments, an anti-PD-1 antibody is administered adjunctive to or with ipilimumab and an antibody-drug conjugate targeting LRRC15 for treating non-small cell lung cancer.

7.7. Dosages and Administration Regimens

The amount of anti-PD-1 antibodies administered will depend upon a variety of factors, including but not limited to, the particular type of solid tumor treated, the stage of the solid tumor being treated, the mode of administration, the frequency of administration, the desired therapeutic benefit, and other parameters such as the age, weight and other characteristics of the patient, etc. Determination of dosages effective to provide therapeutic benefit for specific modes and frequency of administration is within the capabilities of those skilled in the art.

Dosages effective to provide therapeutic benefit may be estimated initially from in vivo animal models or clinical. Suitable animal models for a wide variety of diseases are known in the art.

The anti-PD-1 antibodies disclosed herein may be administered by any route appropriate to the condition to be treated. In some embodiments, the anti-PD-1 antibody is any one of the humanized antibodies listed in TABLE 3. In a specific embodiment, the anti-PD-1 antibody has a heavy chain according to SEQ ID NO:51 or SEQ ID NO:52, and a light chain according to SEQ ID NO:61. An anti-PD-1 antibody will typically be administered parenterally, i.e., infusion, subcutaneous, intramuscular, intravenous (IV), intradermal, intrathecal, bolus, intratumoral injection or epidural ((Shire et al., 2004, *J. Pharm. Sciences* 93(6):1390-1402)). In one embodiment, an anti-PD-1 antibody is provided as a lyophilized powder in a vial. The vials may contain 100 mg, 110 mg, 120 mg, 150 mg, 200 mg, 250 mg, 300 mg, or 400 mg of anti-PD-1 antibody. Prior to administration, the lyophilized powder is reconstituted with sterile water for injection (SWFI) or other suitable medium to provide a solution containing 20 mg/mL anti-PD-1 antibody. In some embodiments, the resulting reconstituted solution is further diluted with saline or other suitable medium for infusion and administered via an IV infusion twice every 7 days, once every 7 days, once every 14 days, once every 21 days, once every 28 days, once every 35 days, once every 42 days, once every 49 days, or once every 56 days. In some embodiments, for the first cycle, the infusion occurs over 90 minutes. In some embodiments, subsequent infusions are over 60 minutes.

In some embodiments, the anti-PD-1 antibody is administered as an IV infusion once every 7 days at 0.1 mg/kg, 0.5 mg/kg, 1.0 mg/kg, 2.0 mg/kg, 3.0 mg/kg, 4.0 mg/kg, 5.0 mg/kg, 6.0 mg/kg, 8.0 mg/kg, or 10.0 mg/kg.

In some embodiments, the anti-PD-1 antibody is administered as an IV infusion once every 14 days at 0.1 mg/kg, 0.5 mg/kg, 1.0 mg/kg, 2.0 mg/kg, 3.0 mg/kg, 4.0 mg/kg, 5.0 mg/kg, 6.0 mg/kg, 8.0 mg/kg, or 10.0 mg/kg.

In some embodiments, the anti-PD-1 antibody is administered as an IV infusion once every 21 days at 0.1 mg/kg, 0.5 mg/kg, 1.0 mg/kg, 2.0 mg/kg, 3.0 mg/kg, 4.0 mg/kg, 5.0 mg/kg, 6.0 mg/kg, 8.0 mg/kg, or 10.0 mg/kg.

In some embodiments, the anti-PD-1 antibody is administered as an IV infusion once every 28 days at 0.1 mg/kg, 0.5 mg/kg, 1.0 mg/kg, 2.0 mg/kg, 3.0 mg/kg, 4.0 mg/kg, 5.0 mg/kg, 6.0 mg/kg, 8.0 mg/kg, or 10.0 mg/kg.

In one exemplary embodiment, an anti-PD-1 antibody is used adjunctive to ipilimumab (YERVOY®) to treat non-small cell lung cancer. The anti-PD-1 antibody is administered via IV infusion once every 21 days at 1.0 mg/kg or 3.0 mg/kg. Ipilimumab is administered by intravenous infusion at a dose of 1 mg/kg once every three weeks for four doses. Subsequent to the last ipilimumab dose, the anti-PD-1 antibody is administered via IV infusion once every 14 days at 1.0 mg/kg or 3.0 mg/kg. The adjunctive anti-PD-1 antibody/ipilimumab therapy is continued until disease progression or no longer tolerated by the patient.

In one exemplary embodiment, an anti-PD-1 antibody is used adjunctive to ipilimumab (YERVOY®) to treat non-small cell lung cancer. The anti-PD-1 antibody is administered via IV infusion once every 14 days at 1.0 mg/kg or 3.0 mg/kg. Ipilimumab is administered by intravenous infusion at a dose of 1 mg/kg once every six weeks for four doses. The adjunctive anti-PD-1 antibody/ipilimumab therapy is continued until disease progression or no longer tolerated by the patient.

In one exemplary embodiment, an anti-PD-1 antibody is used adjunctive to ipilimumab (YERVOY®) to treat non-small cell lung cancer. The anti-PD-1 antibody is administered via IV infusion once every 14 days at 1.0 mg/kg or 3.0 mg/kg. Ipilimumab is administered by intravenous infusion at a dose of 1 mg/kg once every twelve weeks for four doses. The adjunctive anti-PD-1 antibody/ipilimumab therapy is continued until disease progression or no longer tolerated by the patient.

When administered adjunctive to or with other agents, such as other chemotherapeutic agents, the anti-PD-1 antibodies may be administered on the same schedule as the other agent(s), or on a different schedule. When administered on the same schedule, the anti-PD-1 antibody may be administered before, after, or concurrently with the other agent. In some embodiments where an anti-PD-1 antibody is administered adjunctive to, or with, standards of care, the anti-PD-1 antibody may be initiated prior to commencement of the standard therapy, for example a day, several days, a week, several weeks, a month, or even several months before commencement of standard of care therapy. In some embodiments where an anti-PD-1 antibody is administered adjunctive to, or with, standards of care, the anti-PD-1 antibody may be initiated after commencement of the standard therapy, for example a day, several days, a week, several weeks, a month, or even several months after commencement of standard of care therapy.

As will be appreciated by those of skill in the art, the recommended dosages for the various agents described above may need to be adjusted to optimize patient response and maximize therapeutic benefit.

7.8. Exemplary Embodiments

The following are exemplary enumerated embodiments of the present disclosure.

1. An anti-PD-1 binding protein which comprises (i) a $V_H$ chain comprising three CDRs; and (ii) a $V_L$ chain comprising three CDRs, wherein: $V_H$ CDR#1 is GYTFTHYGMN (SEQ ID NO:11); $V_H$ CDR#2 is WVNTYTGEPTYADDFKG (SEQ ID NO:12); $V_H$ CDR#3 is EGEGLGFGD (SEQ ID NO:13); $V_L$ CDR#1 is RSSQSIVHSHGDTYLE (SEQ ID NO:14); $V_L$ CDR#2 is KVSNRFS (SEQ ID NO:15); and $V_L$ CDR#3 is FQGSHIPVT (SEQ ID NO:16).

2. The anti-PD-1 binding protein of embodiment 1, which comprises a $V_H$ chain corresponding in sequence to SEQ ID NO:31; and a $V_L$ chain corresponding in sequence to SEQ ID NO:41.

3. The anti-PD-1 binding protein of embodiment 1, which is humanized.

4. The anti-PD-1 binding protein of embodiment 3, which comprises a $V_H$ chain corresponding in sequence to SEQ ID NO:36; and a $V_L$ chain corresponding in sequence to SEQ ID NO:42.

5. An anti-PD-1 binding protein which comprises (i) a $V_H$ chain comprising three CDRs; and (ii) a $V_L$ chain comprising three CDRs, wherein: $V_H$ CDR#1 is GYTFTHYGMN (SEQ ID NO:11); $V_H$ CDR#2 is WVNTYTGEPTYADDFKG (SEQ ID NO:12); $V_H$ CDR#3 is EGEGMGFGD (SEQ ID NO:23); $V_L$ CDR#1 is RSSQSIVHSHGDTYLE (SEQ ID NO:14); $V_L$ CDR#2 is KVSNRFS (SEQ ID NO:15); and $V_L$ CDR#3 is FQGSHIPVT (SEQ ID NO:16).

6. The anti-PD-1 binding protein of embodiment 5, which comprises a $V_H$ chain corresponding in sequence to SEQ ID NO:33; and a $V_L$ chain corresponding in sequence to SEQ ID NO:42.

7. The anti-PD-1 binding protein of any one of embodiments 1 to 6, which is an IgG.

8. The anti-PD-1 binding protein of embodiment 7, which is an $IgG_1$, optionally comprising a variant CH2 domain comprising the amino acid substitutions L234A and L235A.

9. The anti-PD-1 binding protein of embodiment 7, which is an $IgG_4$, optionally comprising a variant Fc region comprising the amino acid substitution S228P.

10. The anti-PD-1 binding protein of embodiment 8 which comprises a heavy chain corresponding to the sequence of SEQ ID NO:51 or SEQ ID NO:52, and a light chain corresponding to the sequence of SEQ ID NO:61.

11. The anti-PD-1 binding protein of any one of embodiments 1 to 10 which has a $K_D$ of less than about 100 nM.

12. The anti-PD-1 binding protein of embodiment 11 which has a $K_D$ of less than about 10 nM.

13. A pharmaceutical composition comprising the anti-PD-1 binding protein of any one of embodiments 1 to 12, and a pharmaceutically acceptable carrier.

14. A nucleic acid comprising a nucleotide sequence encoding the anti-PD-1 binding protein of any one of embodiments 1 to 12.

15. A vector comprising the nucleic acid of embodiment 14.

16. A prokaryotic host cell transformed with the vector of embodiment 15.

17. A eukaryotic host cell transformed with the vector of embodiment 15.

18. A eukaryotic host cell engineered to express the nucleic acid of embodiment 14.

19. The eukaryotic host cell of embodiment 18 which is a mammalian host cell.

20. A method of producing an anti-PD-1 binding protein thereof, comprising: (a) culturing the host cell of embodiment 17 or embodiment 18 and (b) recovering the anti-PD-1 binding protein.

21. A method of activating the immune system, comprising administering to a patient in need thereof the anti-PD-1 binding protein of any one of embodiments 1 to 12, or the pharmaceutical composition according to embodiment 13.

22. A method of treating a cancer, comprising administering to a patient in need thereof the anti-PD-1 binding protein of any one of embodiments 1 to 12, or the pharmaceutical composition according to embodiment 13.

23. The method of embodiment 22, wherein the cancer is selected from bladder cancer, breast cancer, head and neck cancer, kidney cancer, lung cancer, lymphoma, melanoma, and stomach cancer.

24. The method of embodiment 23, wherein the lung cancer is non-small cell lung cancer.

25. The method of embodiment 22, in which the anti-PD-1 binding protein is administered as a monotherapy.

26. The method of embodiment 22, in which the anti-PD-1 binding protein is administered adjunctive to or with another agent commonly used to treat the cancer.

27. The method of embodiment 26, in which the other agent is selected from radiation, chemotherapy, an antibody drug conjugate, an anti-CD40 antibody, an anti-CTLA-4 antibody and an anti-OX40 antibody.

28. The method of embodiment 27, in which the chemotherapy is cisplatin, carboplatin, paclitaxel, docetaxel, gemcitabine, vinorelbine, vinblastine, irinotecan, etoposide, or pemetrexed, or a pharmaceutically acceptable salt thereof.

29. The method of embodiment 27, in which the antibody drug conjugate targets c-Met kinase.

30. The method of embodiment 27, in which the antibody drug conjugate targets LRRC15.

31. The method of embodiment 27, in which the antibody drug conjugate targets EGFR.

32. The method of embodiment 27, in which the antibody drug conjugate targets CS1.

33. The method of embodiment 27, in which the antibody drug conjugate is rovalpituzumab tesirine.

34. The method of embodiment 27, in which the anti-CTLA-4 antibody is ipilimumab.

8. EXAMPLES

The following Examples, which highlight certain features and properties of embodiments of the anti-PD-1 antibodies described herein are provided for purposes of illustration, and not limitation.

Example 1: Materials and Methods 8.1.1. Antibody Binding to Plate Bound Human PD-1 by ELISA Immunolon 4xHB 96 well plates were coated with 1 ug/ml of human PD-1 Fc fusion in at 4° C. overnight. Plates were blocked with PBS containing 1% BSA for 30 minutes at room temperature and then washed three times with PBS containing 0.1% Tween 20 (PBST) using a plate washer. PD-1-coated plates were then incubated with indicated concentrations of antibodies at room temperature (RT) for one hour. Plates were washed four times with PBST and then incubated for 1 hour at room temperature with 100 μL of goat anti-human Fab fragment specific-biotin prepared to a dilution of 1:5000 in PBS containing 1% BSA. Plates were washed five times in PBST and 100 μL of a 1:1000 dilution of Streptavidin-HRP was added to each well and incubated for 30 minutes at RT. Plates were washed five times in PBST and 100 μL of TMB One Component were added to each well and incubated at RT until color developed (approximately 5-10 minutes). Optical density (OD) was read at 650 nm using Spectromax190 (Molecular Devices).

8.1.2. Antibody Binding to Cell Surface Expressed Human PD-1

PD-1 expressing Jurkat cells were harvested from flasks and resuspended to $2 \times 10^6$ cells/mL in PBS containing 1% BSA. 100 μL of cells were added to a round bottom 96 well plate containing 100 μL of titrated test antibody or isotype control. Cells were incubated with antibodies at room temperature for 25 minutes and then washed twice with PBS containing 1% BSA. The cell pellet was resuspended in 100 μL of a 1:250 diluted secondary antibody goat anti-human Fab PE. Following 25 minutes incubation at RT, cells were washed twice with PBS containing 1% BSA and resuspended in 200 μL of 1% BSA. Cells were analyzed using Becton Dickinson FACSCanto flow cytometer. Data was analyzed using BD FACSDiva software (version 8.0.1).

8.1.3. Antibody Binding to Plate Bound Cynomolgus Monkey PD-1 by ELISA

Immunolon 4xHB 96-well plates were coated with 1 μg/mL of cynomolgus PD-1 Fc fusion in DPBS at 4° C. overnight. Plates were blocked with PBS containing 1% BSA for 30 minutes at RT and then washed three times with PBST (PBS Tween 20 0.1%) using a plate washer. PD-1-coated plates were then incubated with indicated concentrations of antibodies at room temperature for one hour. Plates were washed four times with PBST and then incubated for 1 hour at RT with 100 μL of goat anti-human Fab fragment specific biotin prepared to a dilution of 1:5000 in PBS containing 1% BSA. Plates were washed five times in PBST and 100 μL of a 1:1000 dilution of Streptavidin-HRP was added to each well and incubated for 30 minutes at RT. Plates were subsequently washed five times in PBST and 100 μL of TMB. One component was added to each well and incubated at RT until color developed (approximately 5-10 minutes). Optical density (OD) was read at 650 nm using a Spectromax190 (Molecular Devices).

8.1.4. Antibody Binding to Activated Human CD4+ T Cells

Human peripheral blood mononuclear cells (PBMCs) were isolated from buffy coats purchased from Stanford Blood Center (Palo Alto, Calif.). Briefly, buffy coats were diluted in a 1:1 ratio with PBS without magnesium and calcium. Diluted blood (30 mL) was layered over 15 mL of 90% Ficoll-Paque Plus prepared in PBS without magnesium and calcium contained in SepMate tubes. The tubes were spun at 1200 g for 10 minutes. The interphase was collected and washed twice in 1×PBS. PBMC were cultured at $2\times10^6$ cells/mL for 48 hrs in RPMI media containing 10% HI FCS with 1 µg/mL PHA and 50 U/mL recombinant human IL-2. The cells were collected, washed and incubated with antibodies at RT for 25 minutes. Labeled cells were washed twice with PBS containing 1% BSA. Cells were resuspended in 100 µL of PBS+1% BSA and a 1:250 dilution of PE conjugated goat anti-human Fab fragment and anti-CD4-FITC were added. After 30 minutes, cells were washed twice with PBS containing 1% BSA and resuspended in 200 µL of 1% BSA. Cells were analyzed using Becton Dickinson FACSCanto flow cytometer. Data was analyzed using BD FACSDiva software (version 8.0.1).

8.1.5. Binding Affinity for PD-1 by Surface Plasmon Resonance

The binding kinetics of anti-PD-1 antibodies for recombinant soluble PD-1 ECD (extracellular domain) were determined by surface plasmon resonance-based measurements made on Biacore T200 instrument at 25° C. using an anti-Fc capture assay approach. Recombinant extracellular domains of human PD-1 (residues 1-167) and cynomolgus PD-1 (residues 21-167) were purchased from a commercial source and further purified by gel filtration in 10 mM HEPES, pH 7.4, 150 mM NaCl, 3 mM EDTA. Chip preparation and binding kinetic measurements were made in the assay buffer HBS-EP+ (10 mM HEPES, pH 7.4, 150 mM NaCl, 3 mM EDTA, 0.05% Tween 20). For anti-Fc capture chip preparation, approximately 2000 RU of goat anti-human IgG Fc polyclonal antibody diluted to 25 µg/mL in 10 mM sodium acetate (pH 4.5), was directly immobilized across a CM5 biosensor chip using a standard amine coupling kit according to manufacturer's instructions and procedures. Unreacted moieties on the biosensor surface were blocked with ethanolamine. For binding kinetics measurements, each assay cycle comprises the following steps: (1) capture of test antibody on test surface only; (2) analyte injection (PD-1 ECD or buffer only) over both reference and test surface, 240 µL at 80 µL/min, after which the dissociation was monitored for 900 seconds at 80 µL/min; and (3) regeneration of capture surface by 10 mM glycine hydrochloride, pH 1.5 injections over both reference and test surface. During the assay, all measurements were referenced against the capture surface alone (i.e., with no captured test antibody) and buffer-only injections were used for double referencing. PD-1 injections ranged in concentration from 900 nM to 11.1 nM in a randomized 3-fold dilution series. Data were processed and fitted globally to a 1:1 binding model using Biacore T200 Evaluation software to determine the binding kinetic rate constants, $k_a$ ($M^{-1} \cdot sec^{-1}$) and $k_d$ ($sec^{-1}$), and the equilibrium dissociation constant $K_D$ (M).

8.1.6. Blocking of PD-1 Interaction with PD-L1 and PD-L2

Human PD-1 expressing HEK 293G cells were harvested from confluent flasks. Cells were resuspended in PBS at a concentration of $2\times10^6$ cells/mL. Cells ($1\times10^5$) were added to each well of a 96-well V bottom plate and cells were blocked for 15 min at 4° C. using human FcR block. In separate plates, test antibodies and isotype control solutions were prepared using a 3-fold serial dilution of the 20 µg/mL starting concentration. Cells were washed in 1×PBS and 50 µL of the prepared antibody dilutions and 50 µL of the PD-L1 His-tagged or PD-L2 His-tagged ligands (10 µg/ml) were added to the plate containing cells. Cells were incubated at 4° C. for 30 minutes and washed twice with 1×PBS. Anti-His APC antibody (50 µL) prepared at a dilution of 1:50 in PBS was added to each well and incubated for 30 minutes at 4° C. The cells were washed twice, resuspended in PBS and acquired on LSR II Fortessa (BD Biosciences, San Jose, Calif.).

8.1.7. Allogeneic Human Mixed Lymphocyte Reaction (MLR) Assay Using Purified CD4 T Cells and Dendritic Cells Human PBMCs were isolated from buffy coats purchased from Stanford Blood Center (Palo Alto, Calif.). Briefly, buffy coats were diluted in a 1:1 ratio with PBS without magnesium and calcium. Diluted blood (30 mL) was layered over 15 mL of 90% Ficoll-Paque Plus prepared in PBS without magnesium and calcium contained in SepMate tubes. The tubes were spun at 1200 g for 10 minutes. The interphase was collected and washed twice in 1×PBS. Cells were resuspended at $1\times10^8$ per mL in AIM-V media containing beta mercaptoethanol. Dendritic cells (DCs) were derived by culturing plastic adherent PBMCs in T75 flasks in the presence of 80 ng/mL GM-CSF and 50 ng/mL IL-4 for 7 days. On day 5, 50 pg/mL IL-1α and 200 pg/mL TNF-α was added to the DC cultures. On day 7, DCs were harvested from flasks, irradiated for 7.3 minutes at 414 R/min, and resuspended to a final concentration of $1\times10^5$ cells/mL in complete media (RPMI with L Glutamine containing 10% FBS, lx non-essential vitamins, 1% Pen/Strep solution, 1% sodium pyruvate, 1% HEPES). Allogeneic human CD4 T cells were isolated using the CD4 T cell isolation kit. DCs ($1\times10^4$/well) and purified CD4 T cells ($1\times10^5$/well) were added to a U bottom plate. Test antibody or isotype control (10 µg/mL) was added to the plate containing DCs and T cells. After five days of incubation, supernatant was collected and analyzed for IL-2 and IFN-γ using Milliplex cytometric bead array kit. IFN-γ was measured using Bio-Rad Bioplex System (Bioplex manager 6.0).

8.1.8. Antigen Recall Response to Tetanus Toxoid

Human PBMCs were isolated from buffy coats purchased from Stanford Blood Center as previously described. Cells were resuspended to a final concentration of $2\times10^6$ cells/mL in AIM-V media containing beta mercaptoethanol. PBMCs ($2\times10^5$) were used per well with 0.2 µg/mL tetanus toxoid. Antibody was titrated and the plates were incubated for five days. Supernatants were collected on day 5 and assessed for IFN-γ using a Milliplex cytometric bead array kit. IFN-γ was measured using BioRad Bioplex System (Bioplex manager 6.0).

Example 2: Generation and Humanization of Mouse Anti-PD-1 Antibodies

Mice were immunized according to the methods known in the art (E. Harlow, D. Lane. Antibody: A Laboratory Manual, (Cold Spring Harbor Laboratory Press, Cold Spring Harbor, N.Y., 1998)). Isotype of each monoclonal antibody was determined using the Mouse Isotyping kit (Roche). Hybridoma clones producing antibodies of interest were purified and further characterized for affinity by surface plasmon resonance and ligand competition (ELISA).

Cloning and construction of the expression vector were accomplished by methods known in the art for expression of recombinant monoclonal antibodies.

Humanization of the antibody V region was carried out as outlined by Queen, C. et al. (Proc. Natl. Acad. Sci. USA, 1989; 86:10029-10033). The canonical structures of the CDRs were determined according to Huang et al. (Methods, 2005; 36:35-42). Human variable germline sequences with the same or most similar CDR canonical structures were identified, and appropriate human $V_H$, $V_L$, and J segment sequences were selected to provide the frameworks for the anti-PD-1 variable region. At framework positions in which the computer model suggested significant contact with the CDRs, the amino acids from the murine anti-PD-1 V regions were substituted for the original human framework amino acids (back-mutations). Full amino acid sequences of the $V_H$ and $V_L$ regions of exemplary mouse and humanized antibodies are shown in FIG. 2.

Anti-PD-1 mouse antibody Mu12A11 was humanized according to the method described above. The humanized versions of Mu12A11 $V_H$ were Hu12A11.1b $V_H$ and Hu12A11.2b $V_H$. Hu12A11.1b $V_H$ had $V_H$ 7-4-1 framework regions, with four back mutations of V2I, M48V, F67L, and A93T. Hu12A11.2b $V_H$ had $V_H$ 1-69 framework regions, with seven back mutations of V2I, M48V, V67L, I69F, A71L, E73T, and A93T. Either of the two humanized $V_H$ could be combined with humanized light chain Hu12A11.1a $V_L$ which had $V_L$ 2-28 framework regions, with one back mutation of I2V.

Example 3: Stability of the Anti-PD-1 Antibodies

Stability of exemplary antibodies were determined by measuring PD-1 binding of the antibodies after treatment under oxidative or variable temperature conditions.

An assessment of liability motifs identified a conserved methionine residue at Kabat position 99 (M99) that was believed to be both solvent exposed and prone to deamidation. Samples of the M99 parent antibody Hu12A11.2b1 were exposed to accelerated degradation conditions to enhance potential deamidation (FIG. 3A). The samples treated with 1% hydrogen peroxide (1% HP) or 1% tert-butyl hydroperoxide (1% TBHP) demonstrated loss of binding affinity, suggesting the potential for oxidation of the methionine-99 residue. A set of antibodies containing point mutations at position M99 were constructed, including iso-leucine (M99I, Hu12A11.2b2 having a $V_H$ according to SEQ ID NO:34), valine (M99V, Hu12A11.2b3 having a $V_H$ according to SEQ ID NO:35), and leucine (M99L, Hu12A11.2b4 having a $V_H$ according to SEQ ID NO:36) mutations. The antibody variants were screened for binding to human PD-1 transfected Jurkat cells and $EC_{50}$ values were determined (FIG. 3B). All three point mutation-containing antibodies bound to cell surface PD-1 similarly, but the M99L variant antibody showed higher binding activity as compared to M99V or M99I variants.

The M99L variant Hu12A11.2b4 was found to retain fully binding capacity after temperature stability testing (FIG. 3C). Incubation of Hu12A11.2b4 at −80, 5, 25, or 40° C. afforded no significant loss of activity in terms of $EC_{50}$ or maximal fluorescence intensity (MFI).

Example 4: Binding Affinity of the Anti-PD-1 Antibodies

Table 4-1 below shows in vitro binding affinity data of exemplary antibody Hu12A11.2b4 in comparison to literature anti-PD-1 antibody nivolumab prepared according to the procedures found in U.S. Pat. No. 9,073,994. Hu12A11.2b4 exhibited similar binding properties to PD-1 as compared to nivolumab according to surface plasmon resonance, ELISA assay with human (Hu) or cynomolgus (Cyno) PD-1, or in human Jurkat cells as measured in the assays of Example 1.

TABLE 4-1

Binding Properties of Select Antibodies against PD-1

| Antibody | SPR $K_D$ (M)* | Hu ELISA $EC_{50}$ (pM) | Hu ELISA $OD_{650}$ max | Cyno ELISA $EC_{50}$ (pM) | Hu Jurkat $EC_{50}$ (pM) |
|---|---|---|---|---|---|
| Nivolumab | 2.9E−09 | 101 | 2.2 | 70 | 56 |
| Hu12A11.2b4 | 2.1E−09 | 197 | 2.9 | 102 | 45 |

*SPR = surface plasmon resonance as determined according to Example 1; exponential notation shown (e.g., 3.0E−09 = 3.0 × $10^{-9}$).

Example 5: Biological Activity of Anti-PD-1 Antibody Hu12A11.2b4

Hu12A11.2b4 was evaluated for biological activity in a number of in vitro human cell assays described in Example 1. As shown in Table 5-1, Hu12A11.2b4 demonstrated 180 pM binding to PD-1 in CD4+ T cells. In addition, the anti-PD-1 activity of Hu12A11.2b4 was shown to be mediated at least in part by its ability to block PD-L1 or PD-L2 interaction with PD-1 as assessed by flow cytometry. This biological activity was consistent with the activity of Hu12A11.2b4 in recombinant Jurkat T cells expressing firefly luciferase gene under the control of NFAT response elements with constitutive expression of human PD-1 (Jurkat NFAT assay).

TABLE 5-1

Biological Activity of Exemplary anti-PD-1 Antibodies

| Antibody | CD4+ T-cell binding $EC_{50}$ (pM) | PD-L1 blocking (µg/mL) | PD-L2 blocking (µg/mL) | Jurkat NFAT $EC_{50}$ (µg/mL) |
|---|---|---|---|---|
| Nivolumab | 180 | 0.106 | 0.233 | 15 ± 20 |
| Hu12A11.2b4 | 180 | 0.045 | 0.132 | 4.5 ± 6.5 |

Anti-PD-1 antibody Hu12A11.2b4 further demonstrated an enhancement in immunological response in in vitro assays. As shown in FIG. 4A, treatment with 10 µg/mL of Hu12A11.2b4 in mixed leukocyte cultures effected a significant increase in IL-2 as well as an IFN-γ increase of about 7.4-fold. FIG. 4B shows that Hu12A11.2b4 exhibited a tetanus toxoid recall response of about 6-fold over no antibody treatment at 10 µg/mL, with an $EC_{50}$=161 ng/mL.

The in vitro biological activity observed for Hu12A11.2b4 was similar to that measured for the nivolumab used in Example 4. With respect to immunological response, the comparison antibody nivolumab exhibited an IFN-γ increase of about 5.6-fold in MLR, and a tetanus toxoid recall response of about 6-fold over no antibody treatment at 10 µg/mL, with an $EC_{50}$=218 ng/mL.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An anti-human PD-1 antibody that specifically binds human PD-1 having an amino acid sequence corresponding to SEQ ID NO:1, the antibody comprising (i) a V$_H$ chain comprising three CDRs; and (ii) a V$_L$ chain comprising three CDRs, wherein:

V$_H$ CDR#1 is GYTFTHYGMN (SEQ ID NO:11);
V$_H$ CDR#2 is WVNTYTGEPTYADDFKG (SEQ ID NO:12);
V$_H$ CDR#3 is EGEGLGFGD (SEQ ID NO:13);
V$_L$ CDR#1 is RSSQSIVHSHGDTYLE (SEQ ID NO:14);
V$_L$ CDR#2 is KVSNRFS (SEQ ID NO:15); and
V$_L$ CDR#3 is FQGSHIPVT (SEQ ID NO:16).

2. The anti-human PD-1 antibody of claim 1, which is humanized.

3. The anti-human PD-1 antibody of claim 2, which comprises a V$_H$ chain corresponding in sequence to SEQ ID NO:36; and a V$_L$ chain corresponding in sequence to SEQ ID NO:42.

4. The anti-human PD-1 antibody of claim 3, which is an IgG.

5. The anti-human PD-1 antibody of claim 4, which is an IgG$_1$.

6. The anti-human PD-1 antibody of claim 5 comprising a variant CH2 domain having amino acid substitutions L234A and L235A.

7. The anti-human PD-1 antibody of claim 4, which is an IgG$_4$.

8. The anti-human PD-1 antibody of claim 7 comprising a variant Fc region having an amino acid substitution S228P.

9. The anti-human PD-1 antibody of claim 3 comprising a kappa light constant region.

10. The anti-human PD-1 antibody of claim 3 which comprises a heavy chain corresponding in sequence to SEQ ID NO:51 or SEQ ID NO:52, and a light chain corresponding in sequence to SEQ ID NO:61.

11. A pharmaceutical composition comprising the anti-human PD-1 antibody of claim 1, and a pharmaceutically acceptable carrier.

12. A nucleic acid comprising a nucleotide sequence encoding an anti-human PD-1 antibody that specifically binds human PD-1 having an amino acid sequence corresponding to SEQ ID NO:1 wherein the antibody comprises (i) a $V_H$ chain comprising three CDRs; and (ii) a $V_L$ chain comprising three CDRs, wherein:

$V_H$ CDR#1 is GYTFTHYGMN (SEQ ID NO:11);
$V_H$ CDR#2 is WVNTYTGEPTYADDFKG (SEQ ID NO:12);
$V_H$ CDR#3 is EGEGLGFGD (SEQ ID NO:13);
$V_L$ CDR#1 is RSSQSIVHSHGDTYLE (SEQ ID NO:14);
$V_L$ CDR#2 is KVSNRFS (SEQ ID NO:15); and
$V_L$ CDR#3 is FQGSHIPVT (SEQ ID NO:16).

13. A vector comprising the nucleic acid of claim 12.

14. A prokaryotic host cell transformed with the vector of claim 13.

15. A eukaryotic host cell transformed with the vector of claim 13.

16. A eukaryotic host cell engineered to express the nucleic acid of claim 12.

17. The eukaryotic host cell of claim 16 which is a mammalian host cell.

* * * * *

SEQUENCE LISTING

<160> NUMBER OF SEQ ID NOS: 61

<210> SEQ ID NO 1
<211> LENGTH: 288
<212> TYPE: PRT
<213> ORGANISM: Homo sapiens

<400> SEQUENCE: 1

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 288
<212> TYPE: PRT
<213> ORGANISM: Mus sp.

<400> SEQUENCE: 2

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

```
Arg Ser Leu Thr Phe Tyr Pro Ala Trp Leu Thr Val Ser Glu Gly Ala
            35                  40                  45

Asn Ala Thr Phe Thr Cys Ser Leu Ser Asn Trp Ser Glu Asp Leu Met
 50                  55                  60

Leu Asn Trp Asn Arg Leu Ser Pro Ser Asn Gln Thr Glu Lys Gln Ala
 65                  70                  75                  80

Ala Phe Cys Asn Gly Leu Ser Gln Pro Val Gln Asp Ala Arg Phe Gln
                 85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
            115                 120                 125

His Pro Lys Ala Lys Ile Glu Glu Ser Pro Gly Ala Glu Leu Val Val
130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
            195                 200                 205

Asp Thr Leu Lys Glu Glu Pro Ser Ala Ala Pro Val Pro Ser Val Ala
            210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
            275                 280                 285
```

<210> SEQ ID NO 3
<211> LENGTH: 290
<212> TYPE: PRT
<213> ORGANISM: Homo sapiens

<400> SEQUENCE: 3

```
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125
```

```
Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 4
<211> LENGTH: 262
<212> TYPE: PRT
<213> ORGANISM: Homo sapiens

<400> SEQUENCE: 4

Leu Gln Leu His Gln Ile Ala Ala Leu Phe Thr Val Thr Val Pro Lys
1               5                   10                  15

Glu Leu Tyr Ile Ile Glu His Gly Ser Asn Val Thr Leu Glu Cys Asn
            20                  25                  30

Phe Asp Thr Gly Ser His Val Asn Leu Gly Ala Ile Thr Ala Ser Leu
        35                  40                  45

Gln Lys Val Glu Asn Asp Thr Ser Pro His Arg Glu Arg Ala Thr Leu
50                  55                  60

Leu Glu Glu Gln Leu Pro Leu Gly Lys Ala Ser Phe His Ile Pro Gln
65                  70                  75                  80

Val Gln Val Arg Asp Glu Gly Gln Tyr Gln Cys Ile Ile Ile Tyr Gly
                85                  90                  95

Val Ala Trp Asp Tyr Lys Tyr Leu Thr Leu Lys Val Lys Ala Ser Tyr
            100                 105                 110

Arg Lys Ile Asn Thr His Ile Leu Lys Val Pro Glu Thr Asp Glu Val
        115                 120                 125

Glu Leu Thr Cys Gln Ala Thr Gly Tyr Pro Leu Ala Glu Val Ser Trp
130                 135                 140

Pro Asn Val Ser Val Pro Ala Asn Thr Ser His Ser Arg Thr Pro Glu
145                 150                 155                 160

Gly Leu Tyr Gln Val Thr Ser Val Leu Arg Leu Lys Pro Pro Pro Gly
                165                 170                 175

Arg Asn Phe Ser Cys Val Phe Trp Asn Thr His Val Arg Glu Leu Thr
            180                 185                 190

Leu Ala Ser Ile Asp Leu Gln Ser Gln Met Glu Pro Arg Thr His Pro
        195                 200                 205
```

```
Thr Trp Leu Leu His Ile Phe Ile Pro Ser Cys Ile Ile Ala Phe Ile
    210                 215                 220
Phe Ile Ala Thr Val Ile Ala Leu Arg Lys Gln Leu Cys Gln Lys Leu
225                 230                 235                 240
Tyr Ser Ser Lys Asp Thr Thr Lys Arg Pro Val Thr Thr Thr Lys Arg
                245                 250                 255
Glu Val Asn Ser Ala Ile
                260
```

```
<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Ser Gly Gly Gly Ser Gly Gly Gly Gly Ser
1               5                   10                  15

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Tyr Thr Phe Thr His Tyr Gly Met Asn
1               5                   10

<210> SEQ ID NO 12
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 12

Trp Val Asn Thr Tyr Thr Gly Glu Pro Thr Tyr Ala Asp Asp Phe Lys
1               5                   10                  15

Gly

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Gly Glu Gly Leu Gly Phe Gly Asp
1               5

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Ser Gln Ser Ile Val His Ser His Gly Asp Thr Tyr Leu Glu
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Val Ser Asn Arg Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Gln Gly Ser His Ile Pro Val Thr
1               5

<210> SEQ ID NO 17

<400> SEQUENCE: 17

000

<210> SEQ ID NO 18
```

```
<400> SEQUENCE: 18

000

<210> SEQ ID NO 19

<400> SEQUENCE: 19

000

<210> SEQ ID NO 20

<400> SEQUENCE: 20

000

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Gly Glu Gly Ile Gly Phe Gly Asp
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Gly Glu Gly Val Gly Phe Gly Asp
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Glu Gly Glu Gly Met Gly Phe Gly Asp
1               5

<210> SEQ ID NO 24

<400> SEQUENCE: 24

000

<210> SEQ ID NO 25

<400> SEQUENCE: 25

000

<210> SEQ ID NO 26
```

```
<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Ile Gln Leu Val Gln Ser Gly Pro Glu Leu Lys Lys Pro Gly Glu
1               5                   10                  15

Thr Val Met Ile Ser Cys Lys Ala Ser Gly Tyr Thr Phe Thr His Tyr
            20                  25                  30

Gly Met Asn Trp Val Lys Gln Ala Pro Gly Lys Gly Leu Lys Trp Val
        35                  40                  45

Gly Trp Val Asn Thr Tyr Thr Gly Glu Pro Thr Tyr Ala Asp Asp Phe
    50                  55                  60

Lys Gly Arg Leu Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Thr Arg Glu Gly Glu Gly Met Gly Phe Gly Asp Trp Gly Gln Gly Thr
            100                 105                 110

Thr Leu Thr Val Ser Ser
        115

<210> SEQ ID NO 32
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

```
-continued

<400> SEQUENCE: 32

Glu Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Val
        35                  40                  45

Gly Trp Val Asn Thr Tyr Thr Gly Glu Pro Thr Tyr Ala Asp Asp Phe
    50                  55                  60

Lys Gly Arg Leu Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Thr Arg Glu Gly Glu Gly Met Gly Phe Gly Asp Trp Gly Gln Gly Thr
            100                 105                 110

Thr Val Thr Val Ser Ser
        115

<210> SEQ ID NO 33
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Val
        35                  40                  45

Gly Trp Val Asn Thr Tyr Thr Gly Glu Pro Thr Tyr Ala Asp Asp Phe
    50                  55                  60

Lys Gly Arg Leu Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Glu Gly Met Gly Phe Gly Asp Trp Gly Gln Gly Thr
            100                 105                 110

Thr Val Thr Val Ser Ser
        115

<210> SEQ ID NO 34
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr His Tyr
            20                  25                  30

Gly Met Asn Trp Val Arg Gln Ala Pro Gly Gln Gly Leu Glu Trp Val
```

```
                35                  40                  45
Gly Trp Val Asn Thr Tyr Thr Gly Glu Pro Thr Tyr Ala Asp Asp Phe
     50                  55                  60

Lys Gly Arg Leu Thr Phe Thr Leu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Glu Gly Glu Gly Ile Gly Phe Gly Asp Trp Gly Gln Gly Thr
            100                 105                 110

Thr Val Thr Val Ser Ser
            115

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Ile Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr His Tyr
             20                  25                  30

Gly Met Asn Trp Val Arg Gln Ala Pro Gly Gln Gly Leu Glu Trp Val
         35                  40                  45

Gly Trp Val Asn Thr Tyr Thr Gly Glu Pro Thr Tyr Ala Asp Asp Phe
     50                  55                  60

Lys Gly Arg Leu Thr Phe Thr Leu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Glu Gly Glu Gly Val Gly Phe Gly Asp Trp Gly Gln Gly Thr
            100                 105                 110

Thr Val Thr Val Ser Ser
            115

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Thr His Tyr
             20                  25                  30

Gly Met Asn Trp Val Arg Gln Ala Pro Gly Gln Gly Leu Glu Trp Val
         35                  40                  45

Gly Trp Val Asn Thr Tyr Thr Gly Glu Pro Thr Tyr Ala Asp Asp Phe
     50                  55                  60

Lys Gly Arg Leu Thr Phe Thr Leu Asp Thr Ser Thr Ser Thr Ala Tyr
 65                  70                  75                  80

Met Glu Leu Ser Ser Leu Arg Ser Glu Asp Thr Ala Val Tyr Tyr Cys
```

```
                85                  90                  95
Thr Arg Glu Gly Glu Gly Leu Gly Phe Gly Asp Trp Gly Gln Gly Thr
            100                 105                 110

Thr Val Thr Val Ser Ser
        115

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Val Leu Met Thr Gln Ile Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

His Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ile Pro Val Thr Phe Gly Ala Gly Thr Lys Leu Glu Ile Lys
            100                 105                 110

<210> SEQ ID NO 42
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

His Gly Asp Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Val Thr Phe Gly Gln Gly Thr Lys Leu Glu Ile Lys
            100                 105                 110
```

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

```
Glu Ile Gln Leu Val Gln Ser Gly Ala Glu Val Lys Pro Gly Ser
1               5                   10                  15
Ser Val Lys Val Ser Cys Lys Ala Ser Gly Tyr Thr Phe Thr His Tyr
            20                  25                  30
Gly Met Asn Trp Val Arg Gln Ala Pro Gly Gln Gly Leu Glu Trp Val
        35                  40                  45
Gly Trp Val Asn Thr Tyr Thr Gly Glu Pro Tyr Ala Asp Asp Phe
    50                  55                  60
Lys Gly Arg Leu Thr Phe Thr Leu Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Thr Arg Glu Gly Glu Gly Leu Gly Phe Gly Asp Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
```

```
                370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 52
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Ile Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr His Tyr
                20                  25                  30

Gly Met Asn Trp Val Arg Gln Ala Pro Gly Gln Gly Leu Glu Trp Val
            35                  40                  45

Gly Trp Val Asn Thr Tyr Thr Gly Glu Pro Thr Tyr Ala Asp Asp Phe
        50                  55                  60

Lys Gly Arg Leu Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Glu Gly Glu Gly Leu Gly Phe Gly Asp Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445
```

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

```
<210> SEQ ID NO 60

<400> SEQUENCE: 60

000

<210> SEQ ID NO 61
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

His Gly Asp Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Ile Pro Val Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```